United States Patent
Erichsen

(10) Patent No.: US 11,944,775 B2
(45) Date of Patent: Apr. 2, 2024

(54) ROTATABLE INFUSION DEVICE AND METHODS THEREOF

(71) Applicant: UNOMEDICAL A/S, Birkerod (DK)

(72) Inventor: Jesper Ortld Erichsen, Roskilde (DK)

(73) Assignee: UNOMEDICAL A/S, Lejre (DK)

( * ) Notice: Subject to any disclaimer, the term of this patent is extended or adjusted under 35 U.S.C. 154(b) by 112 days.

(21) Appl. No.: 17/900,262

(22) Filed: Aug. 31, 2022

(65) Prior Publication Data
US 2023/0047582 A1 Feb. 16, 2023

Related U.S. Application Data

(62) Division of application No. 16/877,709, filed on May 19, 2020, now Pat. No. 11,458,292.

(60) Provisional application No. 62/850,468, filed on May 20, 2019.

(51) Int. Cl.
| | | |
|---|---|---|
| *A61M 5/142* | (2006.01) | |
| *A61M 39/10* | (2006.01) | |
| *A61M 5/158* | (2006.01) | |

(52) U.S. Cl.
CPC .... *A61M 39/1055* (2013.01); *A61M 5/14248* (2013.01); *A61M 2005/1587* (2013.01)

(58) Field of Classification Search
CPC .................. A61M 39/1055; A61M 2005/1587
See application file for complete search history.

(56) References Cited

U.S. PATENT DOCUMENTS

| | | | |
|---|---|---|---|
| 6,302,866 B1 | 10/2001 | Marggi | |
| 6,736,797 B1 | 5/2004 | Larsen et al. | |
| 9,216,250 B2 * | 12/2015 | Wyss | ........................ A61P 3/10 |
| 9,675,785 B2 | 6/2017 | Constantineau et al. | |
| 9,757,515 B1 | 9/2017 | Patel | |
| 10,071,210 B2 | 9/2018 | Gray | |
| 10,292,641 B2 | 5/2019 | Bureau et al. | |
| 10,293,101 B2 | 5/2019 | Brewer et al. | |
| 10,369,274 B2 | 8/2019 | OConnor et al. | |
| 10,369,289 B2 | 8/2019 | Cabiri et al. | |
| 10,376,638 B2 | 8/2019 | Levesque et al. | |
| 10,413,661 B2 | 9/2019 | Kamen et al. | |
| 10,432,403 B2 | 10/2019 | Moskal | |
| 10,434,245 B2 | 10/2019 | Yodfat et al. | |
| 10,434,247 B2 | 10/2019 | Cole et al. | |
| 10,434,248 B1 | 10/2019 | Penake et al. | |
| 10,434,253 B2 | 10/2019 | DiPerna et al. | |
| 10,434,285 B2 | 10/2019 | Schoonmaker et al. | |

(Continued)

FOREIGN PATENT DOCUMENTS

| | | |
|---|---|---|
| EP | 3257533 A1 | 12/2017 |
| EP | 3305349 A1 | 4/2018 |

(Continued)

*Primary Examiner* — Laura A Bouchelle
(74) *Attorney, Agent, or Firm* — Taft Stettinius & Hollister LLP; Ryan O. White; Derek B. Lavender

(57) ABSTRACT

An infusion set that has a base having an opening to receive a cannula device, the base having a lower base part and an upper base part, wherein the upper base part is coupled to the lower base part and is rotatable relative to the lower base part and a connector that has a fluid connector tube. The connector prevents the upper base from substantially rotating relative to the lower base and the fluid connector tube is in fluid connection with the cannula device when the connector is coupled to the base.

20 Claims, 30 Drawing Sheets

(56) References Cited

U.S. PATENT DOCUMENTS

| | | |
|---|---|---|
| 10,438,696 B2 | 10/2019 | Shapley et al. |
| 10,441,356 B2 | 10/2019 | Zarins et al. |
| 10,441,713 B1 | 10/2019 | Feldman et al. |
| 10,441,718 B2 | 10/2019 | Tchao et al. |
| 10,441,723 B2 | 10/2019 | Nazzaro |
| 10,441,775 B2 | 10/2019 | Schriver et al. |
| 10,449,290 B2 | 10/2019 | Shapley et al. |
| 10,449,291 B2 | 10/2019 | Hadian et al. |
| 10,449,296 B2 | 10/2019 | Kapas et al. |
| 10,449,306 B2 | 10/2019 | Grover et al. |
| 10,463,572 B2 | 11/2019 | Shor et al. |
| 10,463,785 B2 | 11/2019 | Dewey |
| 10,463,787 B2 | 11/2019 | Shor et al. |
| 10,463,791 B2 | 11/2019 | Shergold et al. |
| 10,471,203 B2 | 11/2019 | Chappel et al. |
| 10,471,206 B2 | 11/2019 | Dittrich |
| 10,478,550 B2 | 11/2019 | Hadvary et al. |
| 10,478,552 B2 | 11/2019 | Cronenberg et al. |
| 10,478,554 B2 | 11/2019 | Bazargan et al. |
| 10,478,555 B2 | 11/2019 | Radojicic |
| 10,481,024 B2 | 11/2019 | Wade et al. |
| 10,483,000 B2 | 11/2019 | Saint et al. |
| 10,485,923 B2 | 11/2019 | Schiendzielorz |
| 10,485,926 B2 | 11/2019 | Vanderveen et al. |
| 10,485,937 B2 | 11/2019 | Yodfat et al. |
| 10,489,617 B2 | 11/2019 | Salem et al. |
| 10,493,201 B2 | 12/2019 | Cole et al. |
| 10,493,202 B2 | 12/2019 | Hayter |
| 10,493,203 B2 | 12/2019 | Yodfat et al. |
| 10,500,352 B2 | 12/2019 | Grant et al. |
| 10,507,316 B2 | 12/2019 | Fielder et al. |
| 10,512,724 B2 | 12/2019 | Renstad et al. |
| 10,525,193 B2 | 1/2020 | Schauderna |
| 10,525,247 B2 | 1/2020 | Bellrichard et al. |
| 10,532,150 B2 | 1/2020 | Bazargan et al. |
| 10,532,151 B2 | 1/2020 | Wei |
| 10,532,155 B2 | 1/2020 | Schiendzielorz |
| 10,532,159 B2 | 1/2020 | Tornsten et al. |
| 10,532,835 B2 | 1/2020 | Chong et al. |
| 10,537,681 B2 | 1/2020 | Tan-Malecki et al. |
| 10,539,481 B2 | 1/2020 | Plahey et al. |
| 10,542,921 B2 | 1/2020 | Kuhn |
| 10,542,936 B2 | 1/2020 | Goldberg et al. |
| 10,549,029 B2 | 2/2020 | Agard et al. |
| 10,549,033 B2 | 2/2020 | Shimizu |
| 10,549,034 B2 | 2/2020 | Eggert et al. |
| 10,549,036 B2 | 2/2020 | Starkweather et al. |
| 10,549,079 B2 | 2/2020 | Burton et al. |
| 10,556,059 B2 | 2/2020 | Cross et al. |
| 10,556,063 B2 | 2/2020 | Murphy, Jr. et al. |
| 10,561,785 B2 | 2/2020 | Roy et al. |
| 10,561,788 B2 | 2/2020 | Roy |
| 10,561,789 B2 | 2/2020 | Mastrototaro et al. |
| 10,561,826 B2 | 2/2020 | Amano et al. |
| 10,561,831 B2 | 2/2020 | Kato |
| 10,569,011 B2 | 2/2020 | Dilanni et al. |
| 10,569,012 B2 | 2/2020 | Schabbach et al. |
| 10,569,014 B2 | 2/2020 | Hanson et al. |
| 10,576,199 B2 | 3/2020 | Sealfon et al. |
| 10,576,203 B2 | 3/2020 | Amon et al. |
| 10,576,204 B2 | 3/2020 | Estes et al. |
| 10,583,241 B2 | 3/2020 | Wu et al. |
| 10,583,247 B2 | 3/2020 | Mandro |
| 10,589,023 B2 | 3/2020 | Cindrich et al. |
| 10,589,028 B2 | 3/2020 | Cabiri et al. |
| 10,596,317 B2 | 3/2020 | Nakanishi |
| 10,596,362 B2 | 3/2020 | Fielder et al. |
| 10,610,638 B2 | 4/2020 | Cabiri et al. |
| 10,610,639 B2 | 4/2020 | Cabiri et al. |
| 10,610,644 B2 | 4/2020 | Mazlish et al. |
| 10,617,817 B2 | 4/2020 | Hwang et al. |
| 10,617,820 B2 | 4/2020 | OConnor et al. |
| 10,625,016 B2 | 4/2020 | Amon et al. |
| 10,625,017 B2 | 4/2020 | Searle et al. |
| 10,625,018 B2 | 4/2020 | Destefano et al. |
| 10,632,248 B2 | 4/2020 | Stefanov et al. |
| 10,632,249 B2 | 4/2020 | Marbet et al. |
| 10,632,253 B2 | 4/2020 | Uchiyama et al. |
| 10,632,256 B2 | 4/2020 | Sasaki |
| 10,632,257 B2 | 4/2020 | Estes et al. |
| 10,635,784 B2 | 4/2020 | Rubalcaba, Jr. et al. |
| 10,639,417 B2 | 5/2020 | Roberts |
| 10,639,418 B2 | 5/2020 | Kamen et al. |
| 10,639,661 B2 | 5/2020 | Fontana |
| 10,646,643 B2 | 5/2020 | Cabiri et al. |
| 10,646,652 B2 | 5/2020 | McCullough et al. |
| 10,646,653 B2 | 5/2020 | Despa et al. |
| 10,653,828 B2 | 5/2020 | Brown et al. |
| 10,653,829 B2 | 5/2020 | Barchen et al. |
| 10,653,833 B2 | 5/2020 | Kamen et al. |
| 10,653,835 B2 | 5/2020 | Dobbles et al. |
| 10,653,846 B2 | 5/2020 | Weibel et al. |
| 10,656,894 B2 | 5/2020 | Fryman |
| 10,661,006 B2 | 5/2020 | Antonio et al. |
| 10,661,007 B2 | 5/2020 | Estes |
| 10,661,008 B2 | 5/2020 | Brewer et al. |
| 10,661,067 B2 | 5/2020 | Kodama |
| 10,668,209 B2 | 6/2020 | Montalvo et al. |
| 10,668,210 B2 | 6/2020 | Kamen et al. |
| 10,668,213 B2 | 6/2020 | Cabiri |
| 10,668,227 B2 | 6/2020 | Caspers |
| 10,675,055 B2 | 6/2020 | Chong et al. |
| 10,675,333 B2 | 6/2020 | Ning et al. |
| 10,675,404 B2 | 6/2020 | Pizzochero et al. |
| 10,682,458 B2 | 6/2020 | Wu et al. |
| 10,682,460 B2 | 6/2020 | Adams et al. |
| 10,682,461 B2 | 6/2020 | Oakes |
| 10,682,463 B2 | 6/2020 | Kamen et al. |
| 10,685,749 B2 | 6/2020 | Hayter et al. |
| 10,688,241 B2 | 6/2020 | Yang |
| 10,688,243 B2 | 6/2020 | Cabiri |
| 10,688,294 B2 | 6/2020 | Cowan et al. |
| 10,709,834 B2 | 7/2020 | Chiu et al. |
| 10,716,891 B2 | 7/2020 | Saab et al. |
| 10,716,893 B2 | 7/2020 | Gray et al. |
| 10,716,895 B2 | 7/2020 | Brewer et al. |
| 10,716,896 B2 | 7/2020 | OConnor et al. |
| 10,716,926 B2 | 7/2020 | Burton et al. |
| 10,719,584 B2 | 7/2020 | Drew |
| 10,722,640 B2 | 7/2020 | McLaughlin |
| 10,722,643 B2 | 7/2020 | Gray et al. |
| 10,722,646 B2 | 7/2020 | Cole et al. |
| 10,722,647 B2 | 7/2020 | Gray |
| 10,722,650 B2 | 7/2020 | Duke et al. |
| 10,722,661 B2 | 7/2020 | Mandro et al. |
| 10,729,842 B2 | 8/2020 | Hooven et al. |
| 10,729,844 B2 | 8/2020 | Cole et al. |
| 10,729,849 B2 | 8/2020 | Finan et al. |
| 10,737,015 B2 | 8/2020 | Estes |
| 10,737,016 B2 | 8/2020 | Smith et al. |
| 10,737,021 B2 | 8/2020 | Deck |
| 10,737,022 B2 | 8/2020 | Mou et al. |
| 10,737,024 B2 | 8/2020 | Schmid |
| 10,737,026 B2 | 8/2020 | Teutsch |
| 10,737,038 B2 | 8/2020 | Cole et al. |
| 10,744,257 B2 | 8/2020 | Mandro et al. |
| 10,751,467 B2 | 8/2020 | Kamen et al. |
| 10,751,468 B2 | 8/2020 | Abal |
| 10,751,476 B2 | 8/2020 | Gazeley et al. |
| 10,751,478 B2 | 8/2020 | Nazzaro |
| 10,757,219 B2 | 8/2020 | Moskal |
| 10,758,675 B2 | 9/2020 | Mazlish et al. |
| 10,758,683 B2 | 9/2020 | Gibson et al. |
| 10,758,721 B2 | 9/2020 | Sonderegger et al. |
| 10,765,801 B2 | 9/2020 | McCullough |
| 10,765,803 B2 | 9/2020 | Gonnelli |
| 10,765,807 B2 | 9/2020 | Allis et al. |
| 10,772,796 B2 | 9/2020 | Kavazov |
| 10,773,019 B2 | 9/2020 | Searle et al. |
| 10,780,215 B2 | 9/2020 | Rosinko et al. |
| 10,780,216 B2 | 9/2020 | Farra |
| 10,780,217 B2 | 9/2020 | Nazzaro et al. |
| 10,780,220 B2 | 9/2020 | Gray |
| 10,780,223 B2 | 9/2020 | Desborough et al. |

(56) References Cited

U.S. PATENT DOCUMENTS

| | | |
|---|---|---|
| 10,792,419 B2 | 10/2020 | Kamen et al. |
| 10,792,424 B2 | 10/2020 | Sasaki |
| 10,792,425 B2 | 10/2020 | Joseph et al. |
| 10,792,440 B2 | 10/2020 | Mandro et al. |
| 10,799,630 B2 | 10/2020 | Mccullough |
| 10,799,631 B2 | 10/2020 | Barmaimon et al. |
| 10,799,632 B2 | 10/2020 | Kohlbrecher |
| 10,806,851 B2 | 10/2020 | Rosinko |
| 10,806,854 B2 | 10/2020 | OConnor et al. |
| 10,806,855 B2 | 10/2020 | Destefano et al. |
| 10,806,859 B2 | 10/2020 | Desborough et al. |
| 10,814,061 B2 | 10/2020 | Bene et al. |
| 10,814,062 B2 | 10/2020 | Gyory |
| 11,690,952 B2 | 7/2023 | Kamen et al. |
| 11,690,953 B2 | 7/2023 | Lawrence et al. |
| 11,696,983 B2 | 7/2023 | Pizzochero et al. |
| 11,701,300 B2 | 7/2023 | Lanier, Jr. et al. |
| 11,702,233 B2 | 7/2023 | Grant et al. |
| 11,707,567 B2 | 7/2023 | Kamen et al. |
| 11,712,513 B2 | 8/2023 | Gray et al. |
| 11,712,517 B2 | 8/2023 | Lawrence et al. |
| 11,717,609 B2 | 8/2023 | Kamen et al. |
| 11,738,138 B2 | 8/2023 | DeStefano et al. |
| 11,738,139 B2 | 8/2023 | Gray |
| 11,752,258 B2 | 9/2023 | Damestani et al. |
| 11,759,565 B2 | 9/2023 | Conrath et al. |
| 2003/0187394 A1 | 10/2003 | Wilkinson et al. |
| 2005/0065466 A1 | 3/2005 | Vedrine |
| 2006/0106346 A1 | 5/2006 | Sullivan et al. |
| 2007/0124002 A1 | 5/2007 | Estes et al. |
| 2007/0191770 A1 | 8/2007 | Moberg et al. |
| 2008/0215035 A1 | 9/2008 | Yodfat et al. |
| 2008/0234630 A1 | 9/2008 | Iddan et al. |
| 2008/0243085 A1 | 10/2008 | DeStefano |
| 2009/0143763 A1 | 6/2009 | Wyss et al. |
| 2009/0326453 A1 | 12/2009 | Adams et al. |
| 2010/0049128 A1 | 2/2010 | McKenzie et al. |
| 2010/0057021 A1 | 3/2010 | Ishikura et al. |
| 2010/0094251 A1 | 4/2010 | Estes |
| 2010/0135831 A1 | 6/2010 | Jacobsen |
| 2010/0145303 A1 | 6/2010 | Yodfat et al. |
| 2010/0168670 A1 | 7/2010 | Srisathapat et al. |
| 2010/0241103 A1 | 9/2010 | Kraft et al. |
| 2011/0029520 A1 | 2/2011 | Leary et al. |
| 2011/0040247 A1 | 2/2011 | Mandro et al. |
| 2011/0112484 A1 | 5/2011 | Carter et al. |
| 2011/0112696 A1 | 5/2011 | Yodfat et al. |
| 2011/0118578 A1 | 5/2011 | Timmerman |
| 2011/0160652 A1 | 6/2011 | Yodfat et al. |
| 2011/0160666 A1 | 6/2011 | Hanson et al. |
| 2011/0313357 A1 | 12/2011 | Skutnik et al. |
| 2012/0014313 A1 | 1/2012 | Chandra et al. |
| 2012/0078170 A1 | 3/2012 | Smith et al. |
| 2012/0136300 A1 | 5/2012 | Schoonmaker et al. |
| 2012/0150123 A1 | 6/2012 | Lawrence et al. |
| 2012/0209085 A1 | 8/2012 | Degen et al. |
| 2012/0238851 A1 | 9/2012 | Kamen et al. |
| 2013/0046239 A1 | 2/2013 | Gonnelli et al. |
| 2013/0046508 A1 | 2/2013 | Sur et al. |
| 2013/0053823 A1 | 2/2013 | Fiering et al. |
| 2013/0060233 A1 | 3/2013 | OConnor et al. |
| 2013/0138075 A1 | 5/2013 | Lambert |
| 2013/0226138 A1 | 8/2013 | Sia |
| 2013/0237955 A1 | 9/2013 | Neta et al. |
| 2014/0025002 A1 | 1/2014 | Qi et al. |
| 2014/0031793 A1 | 1/2014 | Constantineau et al. |
| 2014/0035048 A1 | 2/2014 | Lee et al. |
| 2014/0052096 A1 | 2/2014 | Searle et al. |
| 2014/0054883 A1 | 2/2014 | Lanigan et al. |
| 2014/0127048 A1 | 5/2014 | Dilanni et al. |
| 2014/0128815 A1 | 5/2014 | Cabiri et al. |
| 2014/0163523 A1 | 6/2014 | Constantineau et al. |
| 2014/0276379 A1 | 9/2014 | Uram et al. |
| 2014/0276536 A1 | 9/2014 | Estes |
| 2014/0323961 A1 | 10/2014 | Blomquist et al. |
| 2014/0358112 A1 | 12/2014 | Smith et al. |
| 2015/0025503 A1 | 1/2015 | Searle et al. |
| 2015/0073384 A1 | 3/2015 | Limaye |
| 2015/0080799 A1 | 3/2015 | Schneider et al. |
| 2015/0080800 A1 | 3/2015 | Cronenberg |
| 2015/0105720 A1 | 4/2015 | Montalvo et al. |
| 2015/0112269 A1 | 4/2015 | Sumida et al. |
| 2015/0209505 A1 | 7/2015 | Hanson et al. |
| 2015/0273201 A1 | 10/2015 | Tallarida et al. |
| 2015/0314117 A1 | 11/2015 | Arami et al. |
| 2016/0051750 A1 | 2/2016 | Tsoukalis |
| 2016/0074578 A1 | 3/2016 | Xu et al. |
| 2016/0082182 A1 | 3/2016 | Gregory et al. |
| 2016/0089056 A1 | 3/2016 | Limaye et al. |
| 2016/0089524 A1 | 3/2016 | Anderson |
| 2016/0121046 A1 | 5/2016 | Wyss et al. |
| 2016/0144105 A1 | 5/2016 | Hooven et al. |
| 2016/0193407 A1 | 7/2016 | Qin et al. |
| 2016/0346469 A1 | 12/2016 | Shubinsky et al. |
| 2017/0080157 A1 | 3/2017 | Cabiri et al. |
| 2017/0100542 A1 | 4/2017 | Norton et al. |
| 2017/0232191 A1 | 8/2017 | Smith et al. |
| 2017/0258987 A1 | 9/2017 | Caspers |
| 2017/0290971 A1 | 10/2017 | Hedmann et al. |
| 2017/0296741 A1 | 10/2017 | Gregory |
| 2017/0296742 A1 | 10/2017 | Stefanov |
| 2017/0340827 A1 | 11/2017 | Nazzaro et al. |
| 2017/0340841 A1 | 11/2017 | Sasaki |
| 2017/0351841 A1 | 12/2017 | Moskal |
| 2017/0351851 A1 | 12/2017 | Wang et al. |
| 2017/0368260 A1 | 12/2017 | McCullough et al. |
| 2018/0028744 A1 | 2/2018 | Kim |
| 2018/0036476 A1 | 2/2018 | McCullough et al. |
| 2018/0071450 A1 | 3/2018 | Ruhland |
| 2018/0110420 A1 | 4/2018 | Pekander |
| 2018/0185573 A1 | 7/2018 | Niklaus |
| 2018/0193563 A1 | 7/2018 | Krasnow et al. |
| 2018/0200434 A1 | 7/2018 | Mazlish et al. |
| 2018/0200440 A1 | 7/2018 | Mazlish et al. |
| 2018/0207360 A1 | 7/2018 | Juretich et al. |
| 2018/0214635 A1 | 8/2018 | Raman et al. |
| 2018/0221571 A1 | 8/2018 | Carbone et al. |
| 2018/0228967 A1 | 8/2018 | Hopkins et al. |
| 2018/0271455 A1 | 9/2018 | Zhong et al. |
| 2018/0280607 A1 | 10/2018 | Richards et al. |
| 2018/0280608 A1 | 10/2018 | Gillett et al. |
| 2018/0280619 A1 | 10/2018 | Finan et al. |
| 2018/0291882 A1 | 10/2018 | Algawi et al. |
| 2018/0296757 A1 | 10/2018 | Finan et al. |
| 2018/0344926 A1 | 12/2018 | Brandenburg et al. |
| 2018/0361061 A1 | 12/2018 | Andretta |
| 2018/0372085 A1 | 12/2018 | Velschow et al. |
| 2019/0009019 A1 | 1/2019 | Shor et al. |
| 2019/0009022 A1 | 1/2019 | Oakes |
| 2019/0009023 A1 | 1/2019 | Diperna et al. |
| 2019/0015585 A1 | 1/2019 | Smith |
| 2019/0022317 A1 | 1/2019 | Uddin et al. |
| 2019/0060562 A1 | 2/2019 | Olivas et al. |
| 2019/0083057 A1 | 3/2019 | Saul et al. |
| 2019/0083702 A1 | 3/2019 | Nekouzadeh et al. |
| 2019/0091404 A1 | 3/2019 | Nazzaro et al. |
| 2019/0091417 A1 | 3/2019 | McCaffrey et al. |
| 2019/0111202 A1 | 4/2019 | Falkovich |
| 2019/0117896 A1 | 4/2019 | Booth et al. |
| 2019/0117897 A1 | 4/2019 | Avery et al. |
| 2019/0125226 A1 | 5/2019 | Koya et al. |
| 2019/0175828 A1 | 6/2019 | List et al. |
| 2019/0262535 A1 | 8/2019 | Shubinsky et al. |
| 2019/0275243 A1 | 9/2019 | Deck et al. |
| 2019/0275249 A1 | 9/2019 | von Campenhausen |
| 2019/0282751 A1 | 9/2019 | Della Bidia |
| 2019/0290845 A1 | 9/2019 | List |
| 2019/0298485 A1 | 10/2019 | Forsell |
| 2019/0298912 A1 | 10/2019 | Spencer et al. |
| 2019/0298914 A1 | 10/2019 | Kamen et al. |
| 2019/0298916 A1 | 10/2019 | List |
| 2019/0298918 A1 | 10/2019 | Jallon |
| 2019/0298921 A1 | 10/2019 | Stafford |
| 2019/0298925 A1 | 10/2019 | Cowe et al. |

(56) References Cited

U.S. PATENT DOCUMENTS

| | | |
|---|---|---|
| 2019/0307943 A1 | 10/2019 | Franano et al. |
| 2019/0307954 A1 | 10/2019 | Klemm et al. |
| 2019/0307955 A1 | 10/2019 | Levesque et al. |
| 2019/0307970 A1 | 10/2019 | Kamen et al. |
| 2019/0314572 A1 | 10/2019 | Yang |
| 2019/0321260 A1 | 10/2019 | Grant et al. |
| 2019/0321544 A1 | 10/2019 | List |
| 2019/0321545 A1 | 10/2019 | Saint |
| 2019/0321546 A1 | 10/2019 | Michaud et al. |
| 2019/0321548 A1 | 10/2019 | Cowan |
| 2019/0321552 A1 | 10/2019 | DiPerna et al. |
| 2019/0328963 A1 | 10/2019 | Wolff et al. |
| 2019/0336078 A1 | 11/2019 | Dang et al. |
| 2019/0336678 A1 | 11/2019 | Rule |
| 2019/0336679 A1 | 11/2019 | Staub et al. |
| 2019/0336681 A1 | 11/2019 | Kamen et al. |
| 2019/0336683 A1 | 11/2019 | O'Connor et al. |
| 2019/0341149 A1 | 11/2019 | Chiu et al. |
| 2019/0343434 A1 | 11/2019 | Varsavsky et al. |
| 2019/0344009 A1 | 11/2019 | Damiano et al. |
| 2019/0344010 A1 | 11/2019 | Pizzochero et al. |
| 2019/0344057 A1 | 11/2019 | Cima et al. |
| 2019/0350501 A1 | 11/2019 | Blomquist et al. |
| 2019/0351131 A1 | 11/2019 | Butterfield et al. |
| 2019/0351132 A1 | 11/2019 | Pippin et al. |
| 2019/0351133 A1 | 11/2019 | Grant, Jr. et al. |
| 2019/0351134 A1 | 11/2019 | Cook et al. |
| 2019/0351135 A1 | 11/2019 | Naftalovitz et al. |
| 2019/0351138 A1 | 11/2019 | Bhandar et al. |
| 2019/0351143 A1 | 11/2019 | Egloff et al. |
| 2019/0351209 A1 | 11/2019 | Butziger et al. |
| 2019/0358393 A1 | 11/2019 | Marbet |
| 2019/0358395 A1 | 11/2019 | Olson et al. |
| 2019/0358437 A1 | 11/2019 | Schwartz et al. |
| 2019/0365282 A1 | 12/2019 | Gibson |
| 2019/0365985 A1 | 12/2019 | Zidon et al. |
| 2019/0365986 A1 | 12/2019 | Coiner et al. |
| 2019/0365987 A1 | 12/2019 | Gibson et al. |
| 2019/0365993 A1 | 12/2019 | Staub et al. |
| 2019/0366002 A1 | 12/2019 | Verlaak et al. |
| 2019/0366011 A1 | 12/2019 | Ring |
| 2019/0366012 A1 | 12/2019 | Gross et al. |
| 2019/0368484 A1 | 12/2019 | Chappel et al. |
| 2019/0374434 A1 | 12/2019 | Kamdar et al. |
| 2019/0374706 A1 | 12/2019 | Cabiri et al. |
| 2019/0374707 A1 | 12/2019 | Damestani et al. |
| 2019/0374708 A1 | 12/2019 | Cardinali et al. |
| 2019/0374709 A1 | 12/2019 | Cole et al. |
| 2019/0374711 A1 | 12/2019 | Deliwala |
| 2019/0374714 A1 | 12/2019 | Rioux et al. |
| 2019/0374719 A1 | 12/2019 | Cabiri et al. |
| 2019/0374757 A1 | 12/2019 | Verhoeven et al. |
| 2019/0381238 A1 | 12/2019 | Stonecipher et al. |
| 2019/0381239 A1 | 12/2019 | Cabiri et al. |
| 2019/0381241 A1 | 12/2019 | Bryant et al. |
| 2019/0388609 A1 | 12/2019 | Lanigan et al. |
| 2019/0388612 A1 | 12/2019 | Schramm |
| 2019/0388614 A1 | 12/2019 | Gyrn et al. |
| 2019/0388615 A1 | 12/2019 | Sonderegger et al. |
| 2019/0392938 A1 | 12/2019 | Mermet |
| 2020/0001004 A1 | 1/2020 | Kondo |
| 2020/0001005 A1 | 1/2020 | Politis et al. |
| 2020/0001006 A1 | 1/2020 | Pizzochero et al. |
| 2020/0001007 A1 | 1/2020 | Miesel et al. |
| 2020/0009315 A1 | 1/2020 | Brouet et al. |
| 2020/0009317 A1 | 1/2020 | Cronenberg et al. |
| 2020/0009318 A1 | 1/2020 | Kamen et al. |
| 2020/0009319 A1 | 1/2020 | Ludolph |
| 2020/0009324 A1 | 1/2020 | Barrows et al. |
| 2020/0009331 A1 | 1/2020 | Kamen et al. |
| 2020/0016328 A1 | 1/2020 | Cane et al. |
| 2020/0016329 A1 | 1/2020 | Schabbach et al. |
| 2020/0016330 A1 | 1/2020 | Kapas et al. |
| 2020/0016333 A1 | 1/2020 | Soares et al. |
| 2020/0016335 A1 | 1/2020 | DiPerna et al. |
| 2020/0016336 A1 | 1/2020 | Patek et al. |
| 2020/0023119 A1 | 1/2020 | Barnes et al. |
| 2020/0023121 A1 | 1/2020 | Thomas et al. |
| 2020/0023122 A1 | 1/2020 | Mccullough et al. |
| 2020/0023123 A1 | 1/2020 | O'Connor et al. |
| 2020/0023129 A1 | 1/2020 | Day et al. |
| 2020/0025184 A1 | 1/2020 | Gyory |
| 2020/0027541 A1 | 1/2020 | Xavier et al. |
| 2020/0028914 A1 | 1/2020 | Xavier et al. |
| 2020/0030528 A1 | 1/2020 | Burke et al. |
| 2020/0030529 A1 | 1/2020 | DiPerna et al. |
| 2020/0030530 A1 | 1/2020 | Huang et al. |
| 2020/0030531 A1 | 1/2020 | Day et al. |
| 2020/0030532 A1 | 1/2020 | Day et al. |
| 2020/0030533 A1 | 1/2020 | Day et al. |
| 2020/0030590 A1 | 1/2020 | Buchman et al. |
| 2020/0030592 A1 | 1/2020 | Cheche |
| 2020/0035355 A1 | 1/2020 | Xavier et al. |
| 2020/0038588 A1 | 2/2020 | Varsavsky et al. |
| 2020/0043588 A1 | 2/2020 | Mougiakakou et al. |
| 2020/0046904 A1 | 2/2020 | Schader et al. |
| 2020/0054822 A1 | 2/2020 | Dewey |
| 2020/0054825 A1 | 2/2020 | Kamen et al. |
| 2020/0054826 A1 | 2/2020 | Diianni et al. |
| 2020/0054832 A1 | 2/2020 | Jeong et al. |
| 2020/0061285 A1 | 2/2020 | Reeves |
| 2020/0061287 A1 | 2/2020 | Chappel et al. |
| 2020/0069865 A1 | 3/2020 | Day et al. |
| 2020/0069869 A1 | 3/2020 | Grant et al. |
| 2020/0069871 A1 | 3/2020 | Yavorsky et al. |
| 2020/0069873 A1 | 3/2020 | Pizzochero et al. |
| 2020/0069875 A1 | 3/2020 | Nazzaro et al. |
| 2020/0077340 A1 | 3/2020 | Kruse |
| 2020/0077948 A1 | 3/2020 | Schmid |
| 2020/0078511 A1 | 3/2020 | Focht et al. |
| 2020/0078513 A1 | 3/2020 | Wei |
| 2020/0086041 A1 | 3/2020 | Fuchs et al. |
| 2020/0086042 A1 | 3/2020 | Kamen et al. |
| 2020/0086043 A1 | 3/2020 | Saint |
| 2020/0086044 A1 | 3/2020 | Streit et al. |
| 2020/0086045 A1 | 3/2020 | Azapagic et al. |
| 2020/0086051 A1 | 3/2020 | Grygus et al. |
| 2020/0093980 A1 | 3/2020 | McDermott et al. |
| 2020/0093984 A1 | 3/2020 | Shor et al. |
| 2020/0098463 A1 | 3/2020 | Arunachalam et al. |
| 2020/0098464 A1 | 3/2020 | Velado et al. |
| 2020/0101218 A1 | 4/2020 | Shapley et al. |
| 2020/0101219 A1 | 4/2020 | Wang et al. |
| 2020/0101222 A1 | 4/2020 | Intereur et al. |
| 2020/0101223 A1 | 4/2020 | Lintereur et al. |
| 2020/0101224 A1 | 4/2020 | Lintereur et al. |
| 2020/0101225 A1 | 4/2020 | O'Connor et al. |
| 2020/0101226 A1 | 4/2020 | Rosinko et al. |
| 2020/0108201 A1 | 4/2020 | Ben-David et al. |
| 2020/0108204 A1 | 4/2020 | Mazlish et al. |
| 2020/0111556 A1 | 4/2020 | Schmidlin et al. |
| 2020/0113515 A1 | 4/2020 | O'Connor et al. |
| 2020/0114064 A1 | 4/2020 | Reeves |
| 2020/0114068 A1 | 4/2020 | Schmidlin et al. |
| 2020/0114069 A1 | 4/2020 | Searle et al. |
| 2020/0114072 A1 | 4/2020 | Addiego et al. |
| 2020/0114075 A1 | 4/2020 | Morrow et al. |
| 2020/0114076 A1 | 4/2020 | Ulrich et al. |
| 2020/0114080 A1 | 4/2020 | Barmaimon et al. |
| 2020/0118676 A1 | 4/2020 | Spohn et al. |
| 2020/0121848 A1 | 4/2020 | Schmidlin et al. |
| 2020/0121849 A1 | 4/2020 | Christenson et al. |
| 2020/0121850 A1 | 4/2020 | Christenson et al. |
| 2020/0121854 A1 | 4/2020 | Norton et al. |
| 2020/0121937 A1 | 4/2020 | Yoder et al. |
| 2020/0129692 A1 | 4/2020 | Kim et al. |
| 2020/0135323 A1 | 4/2020 | Bazargan |
| 2020/0138852 A1 | 5/2020 | Chattaraj et al. |
| 2020/0138911 A1 | 5/2020 | Joseph et al. |
| 2020/0139137 A1 | 5/2020 | Crawford |
| 2020/0146938 A1 | 5/2020 | Bourelle et al. |
| 2020/0147298 A1 | 5/2020 | Traverso et al. |
| 2020/0147303 A1 | 5/2020 | Lee |
| 2020/0147304 A1 | 5/2020 | Crouther et al. |

(56) References Cited

U.S. PATENT DOCUMENTS

| | | |
|---|---|---|
| 2020/0147305 A1 | 5/2020 | Estes |
| 2020/0147309 A1 | 5/2020 | Quinn et al. |
| 2020/0155755 A1 | 5/2020 | Chaves et al. |
| 2020/0155757 A1 | 5/2020 | Gregory et al. |
| 2020/0155758 A1 | 5/2020 | Reeves |
| 2020/0164142 A1 | 5/2020 | Poetschke |
| 2020/0164143 A1 | 5/2020 | Cardinali et al. |
| 2020/0164159 A1 | 5/2020 | Chattaraj et al. |
| 2020/0164199 A1 | 5/2020 | Gerlach et al. |
| 2020/0168316 A1 | 5/2020 | Kamen |
| 2020/0171236 A1 | 6/2020 | McCullough et al. |
| 2020/0171294 A1 | 6/2020 | Turner et al. |
| 2020/0179592 A1 | 6/2020 | Adams et al. |
| 2020/0179594 A1 | 6/2020 | Yodfat et al. |
| 2020/0179595 A1 | 6/2020 | McDermott et al. |
| 2020/0179596 A1 | 6/2020 | Dechelette et al. |
| 2020/0179598 A1 | 6/2020 | Penake et al. |
| 2020/0179602 A1 | 6/2020 | Mazlish |
| 2020/0179603 A1 | 6/2020 | Rosinko |
| 2020/0179604 A1 | 6/2020 | Friedli |
| 2020/0179610 A1 | 6/2020 | Bar-El et al. |
| 2020/0188578 A1 | 6/2020 | Bar-El et al. |
| 2020/0188580 A1 | 6/2020 | Gregory et al. |
| 2020/0188581 A1 | 6/2020 | Diianni et al. |
| 2020/0188585 A1 | 6/2020 | Petisce et al. |
| 2020/0188587 A1 | 6/2020 | Sluggett et al. |
| 2020/0188588 A1 | 6/2020 | Estes |
| 2020/0188608 A1 | 6/2020 | Yigal et al. |
| 2020/0197600 A1 | 6/2020 | Chow et al. |
| 2020/0197603 A1 | 6/2020 | Cowe et al. |
| 2020/0197604 A1 | 6/2020 | Friedli |
| 2020/0197621 A1 | 6/2020 | Quinn et al. |
| 2020/0197628 A1 | 6/2020 | McCullough et al. |
| 2020/0206417 A1 | 7/2020 | Yodfat et al. |
| 2020/0206418 A1 | 7/2020 | Gonnelli et al. |
| 2020/0206422 A1 | 7/2020 | Cassim |
| 2020/0206429 A1 | 7/2020 | Hering et al. |
| 2020/0214625 A1 | 7/2020 | Hooven et al. |
| 2020/0215264 A1 | 7/2020 | Searle et al. |
| 2020/0215273 A1 | 7/2020 | Gibson et al. |
| 2020/0222624 A1 | 7/2020 | Destefano et al. |
| 2020/0222625 A1 | 7/2020 | Cabiri et al. |
| 2020/0230313 A1 | 7/2020 | Mojarrad et al. |
| 2020/0230314 A1 | 7/2020 | Kondo et al. |
| 2020/0238003 A1 | 7/2020 | Mgal et al. |
| 2020/0238004 A1 | 7/2020 | Mccullough |
| 2020/0238006 A1 | 7/2020 | Groszmann et al. |
| 2020/0238012 A1 | 7/2020 | Bar-El et al. |
| 2020/0246537 A1 | 8/2020 | Bazargan et al. |
| 2020/0246538 A1 | 8/2020 | Bar-El et al. |
| 2020/0246541 A1 | 8/2020 | Neftel et al. |
| 2020/0253632 A1 | 8/2020 | Chong et al. |
| 2020/0254172 A1 | 8/2020 | Forster et al. |
| 2020/0254173 A1 | 8/2020 | McCullough et al. |
| 2020/0254174 A1 | 8/2020 | Kruse et al. |
| 2020/0254175 A1 | 8/2020 | Roy et al. |
| 2020/0254176 A1 | 8/2020 | Rytz et al. |
| 2020/0261002 A1 | 8/2020 | Pace |
| 2020/0261642 A1 | 8/2020 | Ben-David et al. |
| 2020/0261643 A1 | 8/2020 | Boyaval et al. |
| 2020/0261644 A1 | 8/2020 | Farnan et al. |
| 2020/0261645 A1 | 8/2020 | Kamen et al. |
| 2020/0261649 A1 | 8/2020 | Michaud et al. |
| 2020/0261658 A1 | 8/2020 | Farris et al. |
| 2020/0268962 A1 | 8/2020 | Gamelin |
| 2020/0268965 A1 | 8/2020 | Loudermilk et al. |
| 2020/0268975 A1 | 8/2020 | Kim et al. |
| 2020/0272310 A1 | 8/2020 | Vik et al. |
| 2020/0276384 A1 | 9/2020 | Cabiri et al. |
| 2020/0276386 A1 | 9/2020 | Kamen et al. |
| 2020/0282131 A1 | 9/2020 | Nazzaro |
| 2020/0289743 A1 | 9/2020 | Chiu et al. |
| 2020/0289745 A1 | 9/2020 | Harris et al. |
| 2020/0289748 A1 | 9/2020 | Anigan et al. |
| 2020/0297920 A1 | 9/2020 | McLaughlin |
| 2020/0297923 A1 | 9/2020 | Montalvo et al. |
| 2020/0297927 A1 | 9/2020 | Conrath et al. |
| 2020/0306444 A1 | 10/2020 | Politis et al. |
| 2020/0306445 A1 | 10/2020 | Michaud et al. |
| 2020/0306446 A1 | 10/2020 | Kamen et al. |
| 2020/0306448 A1 | 10/2020 | Schmid |
| 2020/0316290 A1 | 10/2020 | Bourelle et al. |
| 2020/0316291 A1 | 10/2020 | Gibson et al. |
| 2020/0316314 A1 | 10/2020 | Buri et al. |
| 2020/0321094 A1 | 10/2020 | Saint et al. |
| 2020/0324042 A1 | 10/2020 | King et al. |
| 2020/0324048 A1 | 10/2020 | O'Connor et al. |
| 2020/0324101 A1 | 10/2020 | Hartmann et al. |
| 2020/0330679 A1 | 10/2020 | Cronenberg et al. |
| 2020/0330680 A1 | 10/2020 | Deck |
| 2020/0330701 A1 | 10/2020 | Cole et al. |
| 2020/0335194 A1 | 10/2020 | Jacobson et al. |
| 2020/0338257 A1 | 10/2020 | Hooven et al. |
| 2020/0338262 A1 | 10/2020 | Kamen et al. |
| 2020/0338264 A1 | 10/2020 | Allis et al. |
| 2020/0338266 A1 | 10/2020 | Estes |
| 2023/0218823 A1 | 7/2023 | Schmid |
| 2023/0226271 A1 | 7/2023 | Lanigan et al. |
| 2023/0226273 A1 | 7/2023 | Kamen et al. |
| 2023/0226274 A1 | 7/2023 | Kamen et al. |
| 2023/0233756 A1 | 7/2023 | Lanier et al. |
| 2023/0233758 A1 | 7/2023 | Gregory et al. |
| 2023/0241321 A1 | 8/2023 | Olivas et al. |
| 2023/0248920 A1 | 8/2023 | Quinn et al. |
| 2023/0256160 A1 | 8/2023 | Yodfat et al. |
| 2023/0256162 A1 | 8/2023 | Yang |
| 2023/0270936 A1 | 8/2023 | Smith et al. |
| 2023/0270934 A1 | 9/2023 | Thompson et al. |
| 2023/0282328 A1 | 9/2023 | Sadeghzadeh et al. |
| 2023/0293813 A1 | 9/2023 | Diianni et al. |

FOREIGN PATENT DOCUMENTS

| | | |
|---|---|---|
| EP | 3567594 A1 | 11/2019 |
| EP | 3593832 A1 | 1/2020 |
| EP | 3558421 B1 | 7/2023 |
| EP | 3824925 B1 | 7/2023 |
| EP | 3727526 B1 | 8/2023 |
| EP | 3804786 B1 | 8/2023 |
| EP | 4218856 A1 | 8/2023 |
| EP | 2908883 B1 | 9/2023 |
| EP | 3503942 B1 | 9/2023 |
| JP | 2009539437 A | 11/2009 |
| NO | 2020069926 A1 | 4/2020 |
| WO | 2010051079 A2 | 5/2010 |
| WO | 2010084268 A1 | 7/2010 |
| WO | 2015094945 A1 | 6/2015 |
| WO | 2018129519 A1 | 7/2018 |
| WO | 2018210972 A1 | 11/2018 |
| WO | 2018215465 A1 | 11/2018 |
| WO | 2018218082 A1 | 11/2018 |
| WO | 2018222521 A1 | 12/2018 |
| WO | 2018232171 A1 | 12/2018 |
| WO | 2019018838 A1 | 1/2019 |
| WO | 2019022950 A1 | 1/2019 |
| WO | 2019022951 A1 | 1/2019 |
| WO | 2019038751 A1 | 2/2019 |
| WO | 2019043702 A1 | 3/2019 |
| WO | 2019067386 A1 | 4/2019 |
| WO | 2019070472 A1 | 4/2019 |
| WO | 2019074579 A1 | 4/2019 |
| WO | 2019079868 A1 | 5/2019 |
| WO | 2019081947 A1 | 5/2019 |
| WO | 2019186375 A1 | 10/2019 |
| WO | 2019191222 A1 | 10/2019 |
| WO | 2019193089 A1 | 10/2019 |
| WO | 2019197360 A1 | 10/2019 |
| WO | 2019197361 A1 | 10/2019 |
| WO | 2019200198 A1 | 10/2019 |
| WO | 2019213218 A1 | 11/2019 |
| WO | 2019228895 A1 | 12/2019 |
| WO | 2019229686 A1 | 12/2019 |
| WO | 2020005107 A1 | 1/2020 |
| WO | 2020008017 A1 | 1/2020 |

(56) References Cited

FOREIGN PATENT DOCUMENTS

| | | |
|---|---|---|
| WO | 2020011572 A1 | 1/2020 |
| WO | 2020012132 A1 | 1/2020 |
| WO | 2020012308 A1 | 1/2020 |
| WO | 2020013691 A1 | 1/2020 |
| WO | 2020016172 A1 | 1/2020 |
| WO | 2020127181 A1 | 1/2020 |
| WO | 2020025484 A1 | 2/2020 |
| WO | 2020028009 A1 | 2/2020 |
| WO | 2020043459 A1 | 3/2020 |
| WO | 2020046889 A1 | 3/2020 |
| WO | 2020052723 A1 | 3/2020 |
| WO | 2020055785 A1 | 3/2020 |
| WO | 2020068623 A1 | 4/2020 |
| WO | 2020072233 A1 | 4/2020 |
| WO | 2020072234 A1 | 4/2020 |
| WO | 2020072235 A1 | 4/2020 |
| WO | 2020074988 A1 | 4/2020 |
| WO | 2020075042 A1 | 4/2020 |
| WO | 2020104872 A1 | 5/2020 |
| WO | 2020109409 A1 | 6/2020 |
| WO | 2020109417 A1 | 6/2020 |
| WO | 2020112515 A1 | 6/2020 |
| WO | 2020118165 A1 | 6/2020 |
| WO | 2020120511 A1 | 6/2020 |
| WO | 2020141412 A1 | 7/2020 |
| WO | 2020144270 A1 | 7/2020 |
| WO | 2020146306 A1 | 7/2020 |
| WO | 2020148581 A1 | 7/2020 |
| WO | 2020160822 A1 | 8/2020 |
| WO | 2020167537 A1 | 8/2020 |
| WO | 2020193090 A1 | 10/2020 |
| WO | 2020197994 A1 | 10/2020 |
| WO | 2020201270 A1 | 10/2020 |

\* cited by examiner

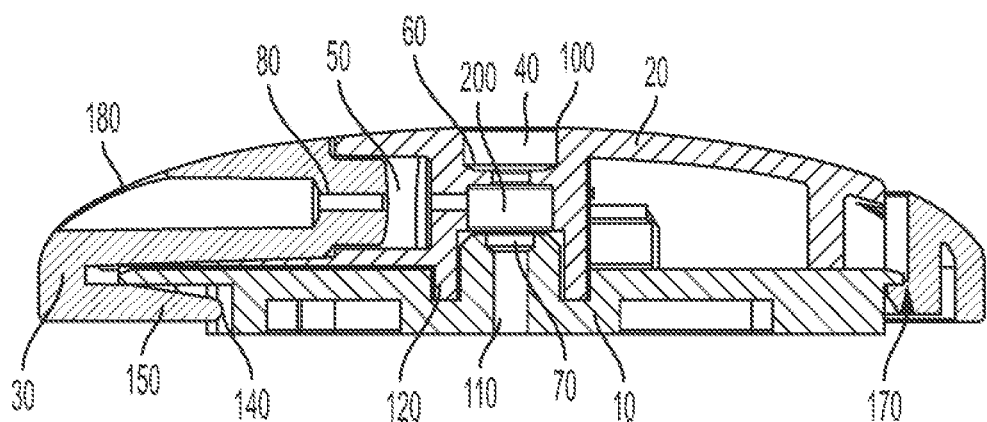
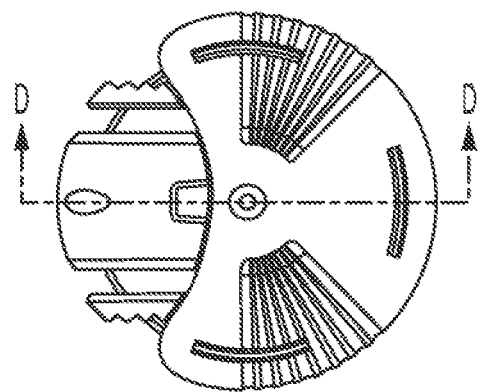
FIG. 5

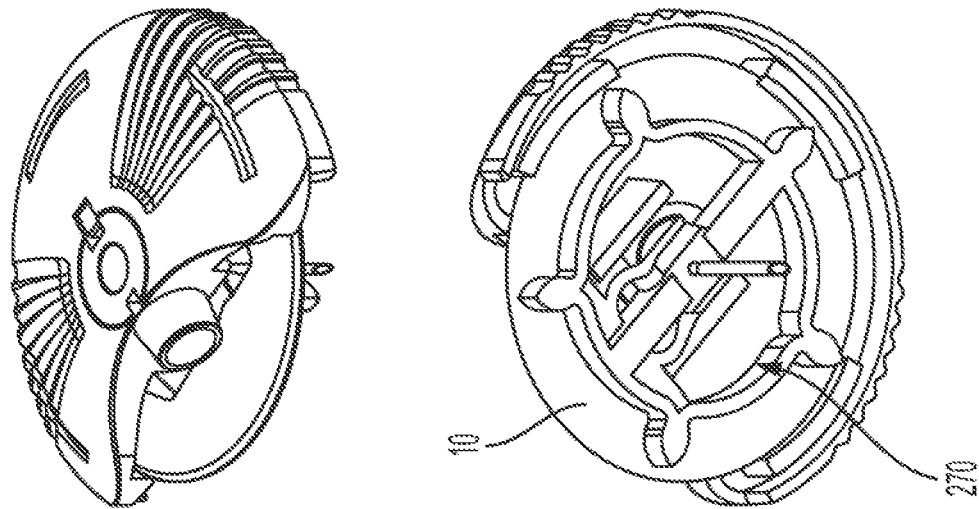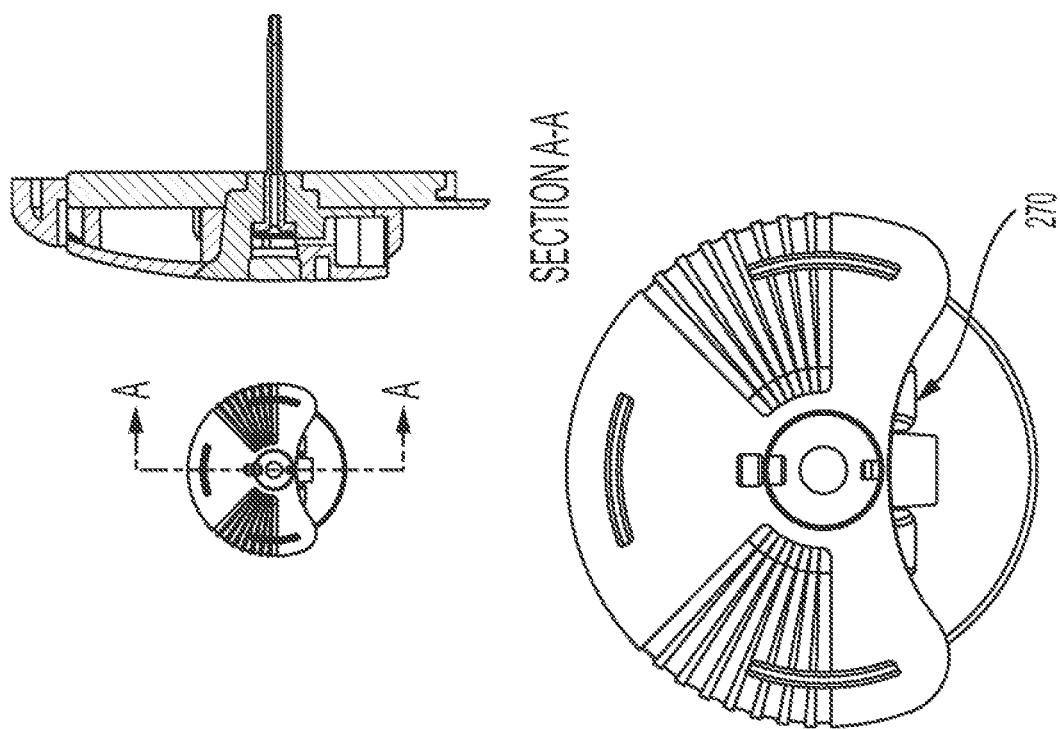
FIG. 19

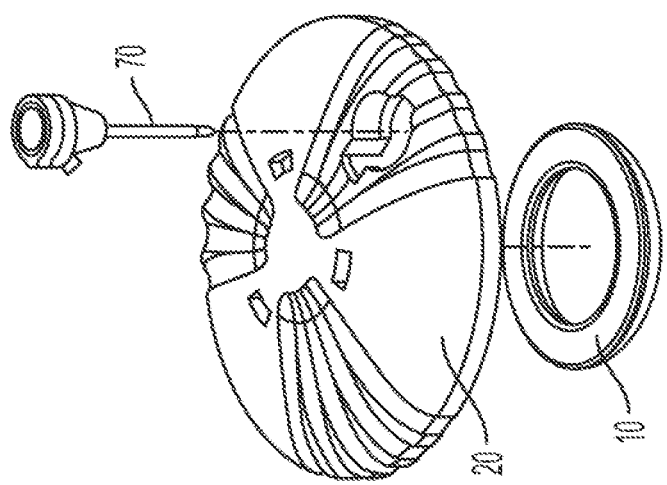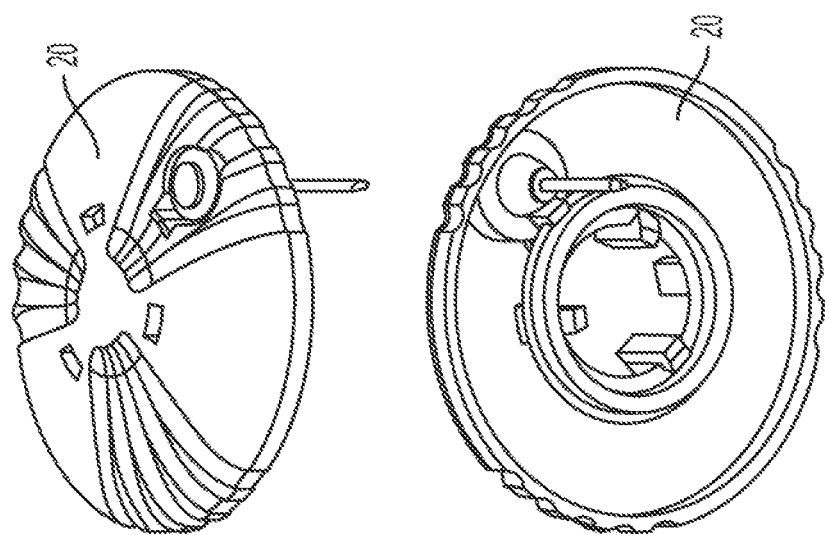
FIG. 25

ROTATABLE INFUSION DEVICE AND METHODS THEREOF

CROSS-REFERENCE TO RELATED APPLICATIONS

The present application is a Divisional of U.S. patent application Ser. No. 16/877,709, filed on 19 May 2020, which claims the benefit of U.S. Provisional Patent Application No. 62/850,468, filed on 20 May 2019, the contents of each of which are incorporated herein by reference in their entirety.

BACKGROUND

Subcutaneous infusion devices allow users to place and use infusion sets outside of a doctor or hospital setting. Infusion devices allow delivery of medications, coupled with subsequent programmable delivery of the medication, including, for example insulin delivery. Parallel monitoring of medication levels is also possible where, for example, sensors are accommodated on the infusion devices.

Re-connection and changing of infusion sets can vary between different systems. In infusion sets having a fixed orientation, a user is presented a single orientation and thus does not need to know how to position a base or a connector of the infusion set for connection. In infusion sets having multiple orientations, a user does not need to position the connector or base in a predefined orientation in order to connect the infusion set to the base. For multiple orientation connections, available devices include fluid orientation infusion sets that connect in parallel to the cannula entering the user (see US 2014/0088550 and US 2017/0185441), fixed orientation, where the device includes predefined orientations for connection usually in the base part (WO 2005/046780, US 2016/0121046, US 2014/0350485), and multiple orientation ports in the connectors, which may be combined into a single or multipart connector (US 2016/0121046 and WO 2005/046780). Connectors have in common a means for helping to guide the connector in place and a means for locking the connector once the connector has been properly positioned.

SUMMARY

Changing an infusion set to allow for continuous delivery of medications can be difficult where orientation of an injection part challenges the user to position the infusion set correctly. The present embodiments disclosed herein solve this problem by providing a rotatable base that allows a connector to be guided into place, allowing fluid communication between the infusion set and the base.

In some embodiments, disclosed herein are infusion sets comprising: a) a base having an opening to receive a cannula device, the base comprising i) a lower base part, and ii) an upper base part, wherein the upper base part is coupled to the lower base part and is rotatable relative to the lower base part; and b) a connector comprising a fluid connector tube and a connection part, wherein the fluid connector tube and the connection part are configured to be in fluid communication, wherein the connector prevents the upper base from substantially rotating relative to the lower base and the fluid connector tube is in fluid connection with the cannula device when the connector is coupled to the base. In some instances, the lower base part does not move once the cannula device is in place. In other instances, the cannula device guides the connector in place when the connector is coupled to the base. In yet other instances, the upper base is rotatable at 360 degrees relative to the lower base. In some instances, the upper base is rotated to a user-friendly position and the connector is coupled to the base to lock the upper base in the user-friendly position.

In some embodiments, the connector comprises at least one snap hook, wherein the snap hook secures the connector to the base when the connector is coupled to the base. In some instances, the lower base comprises a guiding protrusion, wherein the guiding protrusion abuts the snap hook of the connector when the connector is coupled to the base. In yet other instances, the lower base comprises at least one guiding protrusion. In yet other embodiments, the lower base comprises at least three guiding protrusions. In still other instances, the guiding protrusions are radially symmetric.

In some instances, the connector comprises at least one locking protrusion. In some embodiments, the lower base comprises grooves, wherein at least one of the grooves receives the locking protrusion of the connector when the connector is coupled to the base. In yet other embodiments, the lower base comprises at least one groove. In still other embodiments, the lower base comprises at least three grooves. In some embodiments, the grooves of the lower base are radially symmetric.

In some embodiments, the upper base comprises a rotatable connection and the lower base comprises a rotation groove, wherein rotatable connection sits and rotates in the rotation groove. In some instances, the upper base comprises rotation guides, wherein the rotation guides receive the lower base to keep the upper base connected to the lower base and guides the rotation of the upper base relative to the lower base. In some instances, the upper base comprises at least two openings in fluid communication with the cannula device and at least two membranes covering the openings. In still other instances, the membranes comprise an elastomeric material. In some instances, the upper base comprises at least one o-ring, wherein the o-ring provides a fluid seal between the cannula device and the opening of the base, and/or between the cannula device, the upper base and the lower base.

In some embodiments, the cannula device is configured to be inserted into the opening in the base of the infusion devices disclosed herein. the cannula device comprise an cannula housing, wherein the cannula housing is secured by the lower base and wherein the upper base is rotatable relative to the cannula housing. In some embodiments, an opening to receive the cannula device in the upper base decreases in diameter from distal to proximal direction toward the lower base. In some instances, the upper base and the cannula device maintain a fluid seal when the upper base rotates relative to the cannula housing. In yet other instances, the lower base comprises a protrusion to secure the cannula device. In some instances, the cannula device is not rotated when the upper base is rotated relative to the lower base. In some embodiments, the opening in the base for the cannula device is at or near the center of the base. In some instances, the opening in the base for the cannula device is off-center of the base. In some embodiments, the cannula device is placed transdermally through skin of a user. In some embodiments, the fluid connector tube is stainless steel.

In some instances, the connector comprises an opening to receive a connection tube in the infusion devices disclosed herein. In some instances, the lower base comprises an adhesive on a proximal surface, wherein the adhesive secures the base to skin of a user. In one instance, the lower base comprises a clear portion to provide a view of condition of the skin of the user. In another instance, the opening to receive the cannula device in the upper base comprises a tapered coned opening. In still other instances, the connection tube connects to the insulin pump, the external pump, the wearable pump or combinations thereof.

Also disclosed herein are infusions set comprising: a) a base having an opening to receive a cannula device, the base comprising i) a lower base, and ii) an upper base, wherein the upper base is coupled to the lower base and is rotatable relative to the lower base; and b) a cannula device; and a connector comprising a fluid connector tube, wherein the connector prevents the upper base from substantially rotating relative to the lower base and the fluid connector tube is in a fluid connection with the cannula device when the connector is coupled to the base. Incorporation by Reference All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 5: Depicts details of upper base part 20 of the infusion systems disclosed herein.

FIG. 19: Alternative embodiment of the infusion systems disclosed, including a hole for viewing of the skin condition of the patient.

FIG. 25: Alternative embodiments and views of upper base part and lower base part with cannula.

DETAILED DESCRIPTION

Figure 1:
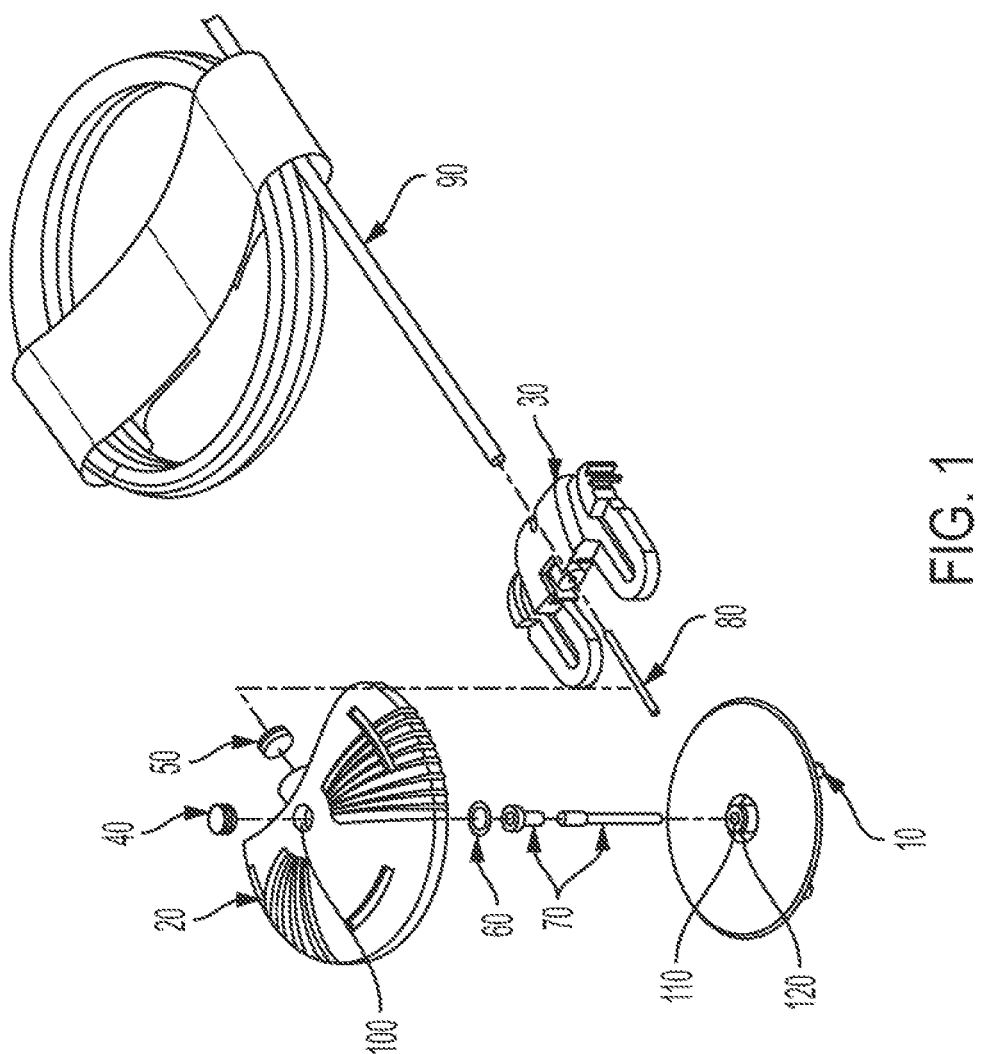
FIG. 1: Depicts a first embodiment of the infusion system, including connection tube 90, connector part 30, lower base part 10 and upper base part 20.

Changing an infusion set to allow for continuous delivery of medications can be difficult where orientation of an injection part challenges a user to position the infusion set correctly. For example, with the extension of infusion set wear time (for example, 3 days to 7 or 10 days), patients use the very same infusion site for much longer durations. As different patients carry their wearable pump at different places during the wear time of an infusion set (for example, in the pocket of a coat or trousers, or in other clothing or placements on the body), it would be advantageous to adjust the site connection angle to the varying places, and by that, ensure product performance and increase patient comfort. The present embodiments disclosed herein solve this problem by providing a rotatable base that allows a connector to be guided into place, allowing fluid communication between the infusion set and the base.

Accordingly, disclosed herein are methods and devices for an infusion set where a user does not require predetermined locations of the base position in order to connect the infusion set to the base. In some embodiments, a means of providing an upper and lower base communicating by way of a circular pathway radially about an axis perpendicular to a proximal surface to the lower base is provided herein. In some instances, the base will rotate into an orientation that makes it capable of guiding the connector into place. In yet other instances, the base comprises at least two parts. In still other instances, the two parts comprise an upper base and a lower base. In yet other instances, the upper base and the lower base are capable of communicating with each other by rotating about a circular pathway. In still other instances, the communication of the upper base and lower base parts radially rotates about an axis perpendicular to a proximal surface to the lower base.

In some embodiments, the rotatable infusion sets disclosed herein do not change the way an end user connects an existing infusion set to a base. The familiarity of the connection interface of the rotatable base part or the connector part to the infusion set for the end user provides ease of use and a lower learning curve for the end user. In some embodiments, an infusion set connects to a rotatable base in the same way the infusion set connects to a non-rotatable base. In other instances, the methods and devices disclosed herein create a multiple orientation infusion set with an already placed cannula housing without limiting the orientation possibilities. In still other instances, the methods and devices disclosed herein provide an infusion set with the functionality of both multiple orientation and inserted cannula housing, while giving the end user the same interactions they are comfortable and experienced with. In still other instances, the methods and devices disclosed herein provide a locking mechanism that partially restricts movement of a part the base. In yet other embodiments, the methods and devices disclosed herein provide a user a substantially covered infusion site that is capable of providing fluid flow to the puncture site. In still other instances, the methods and devices disclosed herein provide to the user a set with a substantially low side profile. In yet other instances, the methods and devices disclosed herein provide a user with an infusion set having an injection port where the set is kept multiple days, with a cannula housing that can be removed and the set turned to provide a fresh site for a new cannula injection port. In still other instances, the methods and devices disclosed herein provide a user with an infusion set comprising a track in the lower base part that guides the upper base part around it.

Provided herein are methods and devices for an infusion set comprising an upper base part and a lower base part, where the base parts connect and are able to move relative to one another. In some embodiments, the movement of the base parts is a circular pathway about an axis perpendicular to a proximal surface, to the lower base. In some instances, the proximal surface refers to the surface that is closer to a skin surface of a user. In some instances, the upper base part can rotate freely relative to the lower base part. In some instances, the upper base part can rotate 360 degrees relative to the lower base part. In some instances, the upper base part can rotate at least 90, 180, or 270 degrees relative to the lower base part.

Provided herein are rotatable infusion systems or devices comprising a base and a connector. In some embodiments, the base comprises a lower base part and an upper base part. In some instances, the lower base part holds catheter and has a surface that adheres to the skin of the user using an adhesive. In some instances, the upper base part can freely rotate to the desired orientation. In some instances, the upper base part can rotate 360 degrees relative to the lower base part. In some cases, the upper base part is oriented after the infusion system is placed on the user. In some cases, the upper base part is oriented before a catheter or a cannula device is placed on the user. In some instances, the lower and upper base parts form a sealed chamber that is sealed by at least one membrane and o-rings. In some instances, there are two membranes that seal the sealed chamber. In some instances, the membrane comprises a self-sealing material. In some instances, the membrane comprises an elastomeric polymer. In some instances, the membrane comprises silicone. In some instances, the o-rings comprise a compressible material. In some instances, the o-rings comprise an elastomeric polymer. In some instances, the o-rings comprise silicone. The membranes and o-rings help to ensure a good seal of the fluid connection that when the connector is coupled to the base parts a free flow of the fluid (e.g. medication, insulin) is provided to the user. In some embodiments, the fluid comprises a medication. In some embodiments, the fluid comprises insulin.

In some embodiments, the base part comprises multiple parts that are assembled for use. In some instances, the base comprises a lower part, an upper base part, and a cannula housing, where the base parts secure the infusion set. The lower base part has a surface that adheres to the skin of the user using an adhesive. The cannula housing can be inserted into the base parts using an opening in the base parts for the cannula housing when the patient is applying the infusion set, which hides the needle from the user. Hiding the needle from the view of the user can help alleviate anxiety or discomfort in the user in inserting a needle into their skin. In some embodiments, the cannula housing comprises guides for insertion, a space for cannula insertion, or a fastener. In some embodiment, the lower base part comprises arms for retaining cannula housing, which secures the cannula housing in position and maintains its orientation. In some embodiments, the cannula housing forms a sealed chamber with the upper base part when inserted into the base parts. In some embodiments, the sealed chamber is sealed by membranes and is in fluid communication with a medication reservoir only when the connector is coupled to the base parts and the fluid connector tube penetrates through the membrane to establish a fluid communication with the sealed chamber. In some embodiments, when the connector is coupled to the base parts having a cannula housing, the medication (e.g. insulin) from the reservoir can flow to through the fluid path to the user. In some embodiments, the upper base part allows the infusion set to freely orientate after the infusion set has been placed on the user. In some embodiments, the upper base part allows the infusion set to freely orientate before the infusion set has been placed on the user.

In various embodiments disclosed herein, the various base parts are coupled to each other by a number of mechanisms. In some embodiments, the upper and the lower base parts connect to each other by with at least one central placed snap-hook. Alternatively or in combination, the upper and the lower base parts connect to each other by at least one edge placed snap hook. In some embodiments, the upper and the lower base parts connect to each other by a plurality of edge placed snap hook.

The connector disclosed herein comprises of a connector body, a fluid connector tube, a connection tube, and an opening for the connection tube. In some embodiment, the fluid connector tube is a steel cannula. In some embodiments, the fluid connector tube penetrates one of the membranes on the upper base part. In some embodiments, the connection tube inserts through an opening in the connector body and forms a fluid connection with the fluid connector tube. In some embodiments, the connection tube connects to an insulin pump, providing the user with insulin.

The infusion set disclosed herein comprises a sealed chamber. In some embodiments, the sealed chamber is formed in a cavity in the upper base part that is bound by membranes and the cannula device.

In some cases, the rotatable base parts are designed to be compatible with existing infusion sets. In some instances, the rotatable base parts are compatible with commonly used methods to connect the infusion set to the base parts. In some instances, the connector part provides the site for connecting the infusion set to the base parts.

In some embodiments, the infusion set connects to the base using a connector tube placed into an opening in a body of a connector that is already coupled to the base. In some embodiments, the infusion set connects to the base by coupling the connector to the base, where the connector is connected to the infusion set by a connection tube before the connector couples to the base.

The methods and devices disclosed herein provide an infusion set with the functionality of both multiple orientation and inserted cannula housing, while giving the end user the same interactions they are comfortable and experienced with. In some instances, the methods and devices provide an infusion set where the user can easily change the orientation of the infusion set without changing the infusion set or dislodging the infusion set from the skin surface of the user. In some embodiments, the dimensions, including but not limited to height, width, length, and shape, of the rotatable infusion set is substantially similar to that of a non-rotatable infusion set. The similar dimensions between the rotatable infusion set and the non-rotatable infusion set may aid the user by providing familiarity of use and wear.

In some instances, the methods and devices disclosed herein provide a locking mechanism that partially restricts movement of a part the base. In some embodiments, the infusion set comprises a connector having a locking protrusion that partially restricts movement of a part the base. In some embodiments, the locking protrusion of the connector fits into one of the grooves in between the guiding protrusion parts on one of the surfaces of the lower base part when the connector is coupled to the base parts. In some embodiments, the snap hooks of the connector fits securely into the openings of the upper base part. When the connector is coupled to the base parts, the locking protrusion fits into the groove of the lower base part and the snap hooks fit into the upper base part, thereby restricting the movement of the base parts relative to each other. In some embodiments, the locking mechanism comprises the locking protrusion. Alternatively or in combination, the locking mechanism comprises the snap hooks. In some embodiments, the locking mechanism restricts the movement of the base parts completely. In some embodiments, the complete restriction of the movement of the base parts refers to movement of near 0 degrees of rotation. In some embodiments, the locking mechanism restricts the movement of the base parts partially. In some embodiments, the partial restriction of the movement of the base parts refers movement of no more than 5 degrees, 10 degrees, 15 degrees, 20 degrees, 25 degrees, 30 degrees, 35 degrees, 40 degrees, or 45 degrees of rotation.

In some instances, the methods and devices disclosed herein provide a user a substantially covered infusion site that is capable of providing air flow to the skin around the infusion site. The infusion set partly covers the skin around the infusion site to allow the skin to breathe and reduce skin irritation while having enough of a contact surface area to provide a good adhesive seal of the infusion set to the skin around the infusion site. In some embodiments, the proximal surface of the infusion set in contact with the skin of the user partly covers the skin near the infusion site. In some embodiments, the proximal surface of the infusion set covers at least 50%, 60%, 70%, 80%, 90%, 95%, 99% of the infusion site. In some embodiments, the proximal surface of the infusion set covers no more than 50%, 60%, 70%, 80%, 90%, 95%, 99% of the infusion site. In some embodiments, the proximal surface of the infusion set has at least one hole or opening on the lower base part to provide a view of the skin of the user. In some embodiments, the upper base part also has at least one hole or opening to view the skin of the user. In some embodiments, the hole or opening on the lower base part is covered with a clear or transparent material. In some embodiments, the hole or opening on the lower base part is covered with a breathable material. The opening allows the user to view the condition of the skin without disconnecting the infusion set from the skin.

In some embodiments, the infusion set covers various distances away and over the infusion site. In some embodiments, the infusion set covers at least 1 cm, 2 cm, 3 cm, 4 cm, 5 cm, 6 cm, 7 cm, 8 cm, 9 cm, or 10 cm away from the infusion site on the skin of the user.

In some instances, the methods and devices disclosed herein provide to the user a set with a substantially low side profile. The low side profile of the infusion set allows the infusion set to be close to the skin of the user and provides a less obtrusive wear for an extended period of time for the user. In some embodiments, the infusion set has a side profile of no more than 1 cm, 2 cm, 3 cm, 4 cm, 5 cm, 6 cm, 7 cm, 8 cm, 9 cm, 10 cm, 11 cm, 12 cm, 13 cm, 14 cm, or 15 cm. In some embodiments, the infusion set has a side profile of at least 1 cm, 2 cm, 3 cm, 4 cm, 5 cm, 6 cm, 7 cm, 8 cm, 9 cm, 10 cm, 11 cm, 12 cm, 13 cm, 14 cm, or 15 cm.

In some instances, the methods and devices disclosed herein provide a user with an infusion set having an injection port where the set is kept multiple days, with a cannula housing that can be removed and the set turned to provide a fresh site for a new cannula injection port. In some embodiments, the infusion set is kept for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 30 days at a single infusion site. In some embodiments, the infusion set is kept for at least 1 week, 2 weeks, 3 weeks, or 4 weeks at a single infusion site. In some embodiments, the infusion set is kept for no more than 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or 30 days at a single infusion site. In some embodiments, the infusion set is designed to maintain sterility and fluid seal for the predetermined, extended period of use.

In some instances, the lower base part has grooves for coupling to the locking protrusion of the connector. In some embodiments, the grooves are radially symmetric. In some embodiments, the grooves are not radially symmetric. In some embodiments, the lower base part has at least 1, 2, 3, 4, 5, 6, 7, 8, 9, or 10 grooves. In some embodiments, the lower base part has no more than 2, 3, 4, 5, 6, 7, 8, 9, or 10 grooves. In some embodiments, the lower base part has 1, 2, 3, 4, 5, 6, 7, 8, 9, or 10 grooves. In some embodiments, the grooves are sized to be close to the dimension of the locking protrusion of the connector. In some embodiments, having grooves that are sized to be close to the dimension of the locking protrusion of the connector substantially limits the rotattion of the base parts after the connector is coupled to the base parts.

In some instances, the lower base part has guiding protrusions for forming the grooves that couple to the locking protrusion of the connector. In some embodiments, the guiding protrusions are radially symmetric. In some embodiments, the guiding protrusions are not radially symmetric. In some embodiments, the lower base part has at least 1, 2, 3, 4, 5, 6, 7, 8, 9, or 10 guiding protrusions. In some embodiments, the lower base part has no more than 2, 3, 4, 5, 6, 7, 8, 9, or 10 guiding protrusions. In some embodiments, the lower base part has 1, 2, 3, 4, 5, 6, 7, 8, 9, or 10 guiding protrusions.

In some instances, the upper base part has a rotation guides for keeping the upper base part connected to the lower base part. The rotation guides may hook onto the perimeter of the lower base part. In some embodiments, the rotation guides are continuous along the perimeter of the upper base part. In some embodiments, the rotation guides are not continuous along the perimeter of the upper base part. In some embodiments, the rotation guides are radially symmetric. In some embodiments, the rotation guides are not radially symmetric. In some embodiments, the upper base part has at least 1, 2, 3, 4, 5, 6, 7, 8, 9, or 10 rotation guides. In some embodiments, the upper base part has no more than 2, 3, 4, 5, 6, 7, 8, 9, or 10 rotation guides. In some embodiments, the upper base part has 1, 2, 3, 4, 5, 6, 7, 8, 9, or 10 rotation guides.

In some instances, the fluid connector tube on the connector has a diameter compatible medical grade tubes commonly used for infusion sets. In some embodiments, the fluid connector tube is 23 gauge, 24 gauge, 25 gauge, 26 gauge, 27 gauge, 28 gauge, 29 gauge, 30 gauge, 31 gauge, 32 gauge, or 33 gauge.

In some instances, the cannula on the cannula device has various diameters. In some embodiments, the cannula is 23 gauge, 24 gauge, 25 gauge, 26 gauge, 27 gauge, 28 gauge, 29 gauge, 30 gauge, 31 gauge, 32 gauge, or 33 gauge.

The lower base part and the upper base part may be various sizes relative to each other. In some embodiments, the lower base part and the upper base part have similar diameters. In some embodiments, the lower base part is smaller in diameter than the upper base part. In some embodiments, the lower base part comprises a back tap to prevent the lower base part from tipping or wobbling relative to the upper base part. In some embodiments, the lower base part has sufficient contact area to adhere to the skin of the user. In some embodiments, the connector has a shortened notch to allow the lower base part to have a larger contact area.

In some embodiments, the cannula device is held by a cannula housing. In some embodiments, the cannula housing is inserted in to the base parts. In some embodiments, the cannula housing is integrated in to the base parts. In some embodiments, the cannula of the cannula device does not turn as the orientation of the base part changes. In some embodiments, coupling of the connector does not damage the seal of the fluid chamber. In some embodiments, the cannula does not turn after it has been inserted into the skin of the user. In some embodiments, the cannula housing is locked and secured by the locking arms on the lower base part. Alternatively or in combination, the cannula housing is not locked around the central axis by the upper base part. In some embodiments, the upper base part has a coned collar to help secure the cannula housing. Alternatively or in combination, the upper bas part has a recessed portion to align the cannula house for insertion. In some embodiments, the cannula housing comprises a collar to protect the cannula device body. In some embodiments, the cannula housing is compatible with an inserter, which can be used to place the cannula device and cannula housing into the base parts. In some embodiments, the cannula housing forms a sealed chamber in the upper base part, where the fluid seal of the sealed chamber is secured by at least one o-ring. In some embodiments, two o-rings secure the fluid seal. In some embodiments, the cannula housing comprises at least one of a fastener, a tab, or a protrusion part to help secure the cannula housing to the base parts. In some embodiments, the fastener comprises a flexible material. In some embodiments, the fastener comprises a plastic. In some embodiments, the protrusion part sits on a recessed portion of the lower base part. EXAMPLES FIG. 1 depicts a first embodiment of the infusion systems disclosed herein. Connection tube 90 connects with connector 30, which is fluidly connected to fluid connector tube 80. Fluid connector tube 80 connects to upper base 20, which includes a first membrane 50, which maintains fluid connection between the upper base part 20 and connection tube 90 via connector 30. Upper base part 20 connects to lower base part 10, via second membrane 40, o-ring 60 within opening 100 on upper base. Lower base part 10 aligns with upper base part 20 through hole 110 and rotation groove 120 through which a cannula device 70 passes through upper base part 20 and lower base part 10 and inserts into patient.

Figure 2:
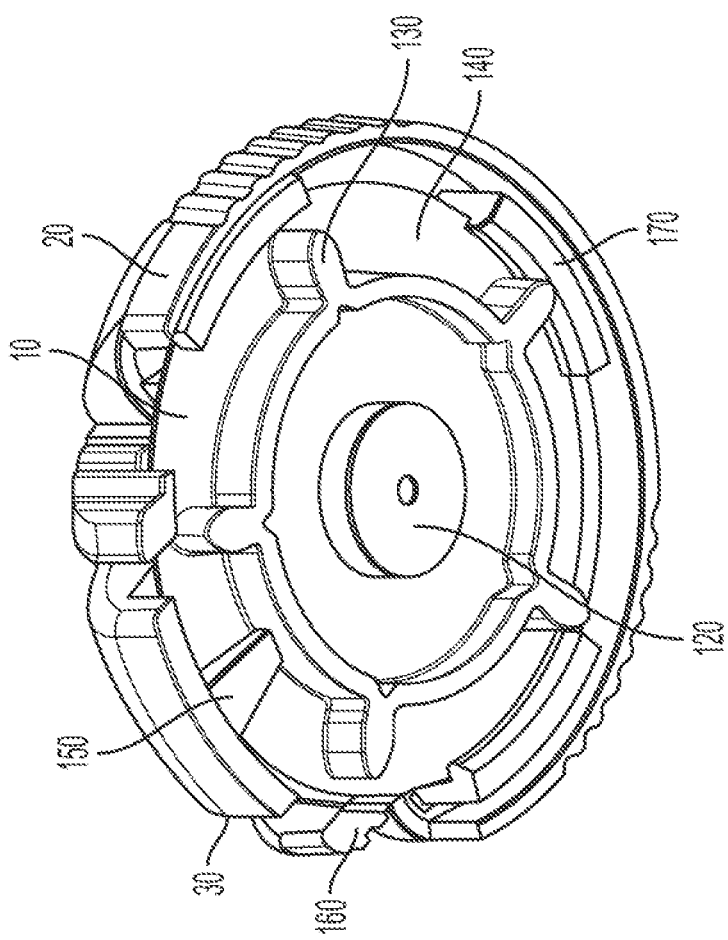
FIG. 2: Depicts details of lower base part 10 of the infusion systems disclosed herein.

FIG. 2 depicts further details of the connector 30, lower base part 10 and upper base part 20. The assembled infusion system is shown from underneath the lower base part 10. Locking protrusion 150 on connector 30 limits movement of lower base part 10 and guiding protrusion parts 130 via grooves within lower base part 10 and rotation groove 120. Snap hook 160 on connector 30 secures upper base part 20 and lower base part 10 in the infusion system and allows fluid connection to connection tube (not shown). Upper base part includes rotation guides 170 to further limit movement of the infusion device while allowing swiveling of the upper base part within the device.

Figure 3:
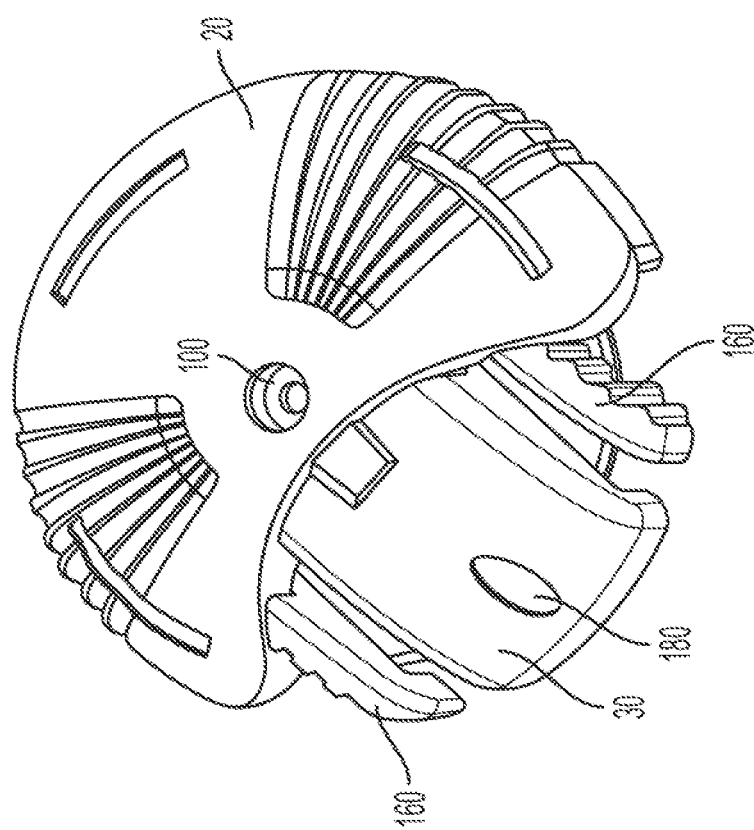
FIG. 3: Depicts details of upper base part 20 of the infusion systems disclosed herein.

FIG. 3 depicts further details of the connector 30, lower base part 10 and upper base part 20 of the assembled infusion system as shown from the top or opposite side of FIG. 2. The connector 30 is inserted in to the lower base part 10 that is aligned with the upper base part 20, where the snap hooks 160 of the connector 30 help to secure the connector to the lower base part 10 and upper base part 20. The opening for connection tube 180 on the connector may receive the connection tube 90, in order to have the connection tube 90 in fluid connection to the fluid connector tube 80 and the cannula device 70 when the connector 30 is coupled to the lower and upper base parts 10, 20. In some cases, the opening of the cannula device on the upper base part 100 allows placing a cannula device 70 to the base parts. In some cases, the opening of the opening of the cannula device on the upper base part 100 is covered by a membrane 70.

Figure 4:
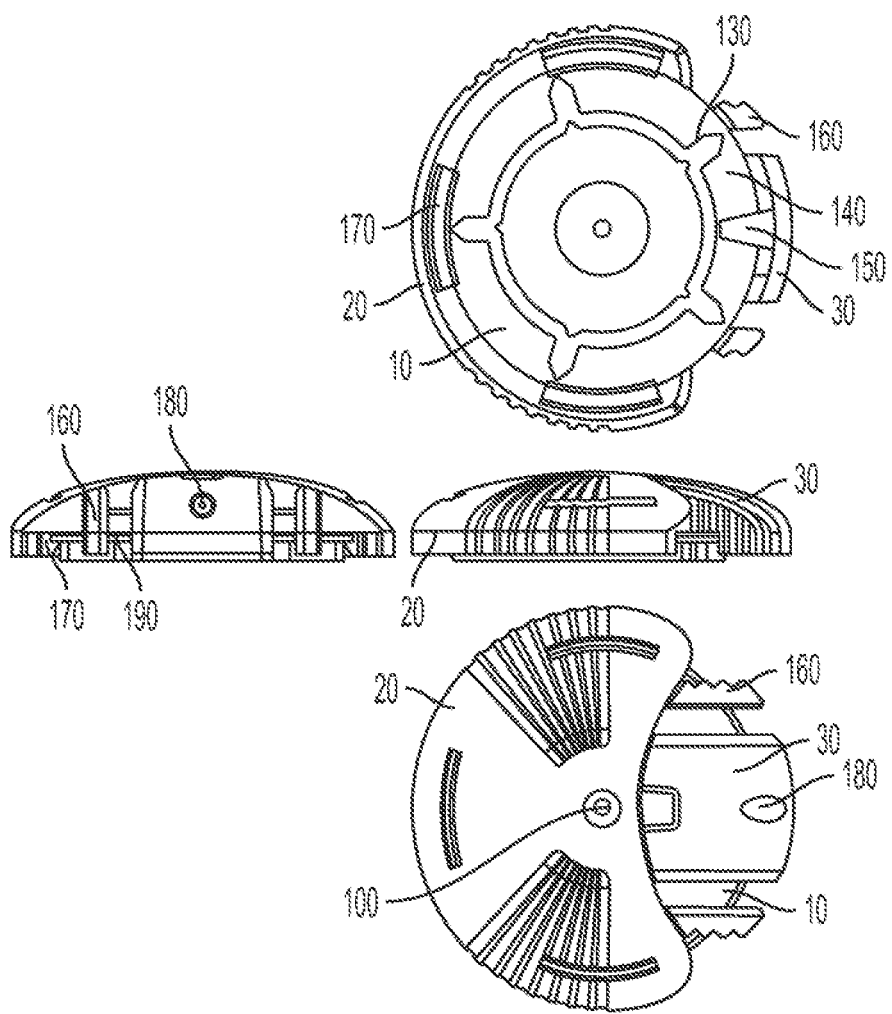
FIG. 4: Depicts alternate views of lower base part 10 and upper base part 20 of the infusion systems disclosed herein.

FIG. 4 depicts various views of an embodiment of the assembled infusion systems disclosed herein. The top image shows a view from underneath the lower base part 10. The lower base part 10 is aligned with the upper base part 20, and the aligned base parts are coupled to the connector 30. The rotation guides 170 of the upper base part 20 helps to secure the alignment of the upper base part 20 to the lower base part 10 and limit the wobbling of the lower base part 10 relative to the upper base part 20. The locking protrusion 150 of the connector 30 helps to limit the rotation of the lower base part 10 when placed in the groove 140 in between the guiding protrusion parts 130 of the lower base part 10. The snap hooks 160 of the connector 30 helps to secure the connector in the aligned base parts. The side view of the assembled infusion systems show an opening for the connection tube 180 on the connector 30 that can be inserted with a connection tube connected to a medication reservoir. The side view also shows guides 190 on the upper base part for coupling of the connector, snap hooks 160 on the connector that fit into the assembled base parts, and the rotation guides 170 on the upper base part 20 that wraps around the edge of the lower base part 10. The view from the top shows the upper base part 20 having an opening for a cannula device 100, the lower base part 10, and the connector 30 having an opening for connection tube 180 and snap hooks 160 that is coupled to the base parts.

FIG. 5 depicts a cross-sectional view of an embodiment of the infusion system across the section line D-D. The cross-sectional view shows inner cavities within the assembled infusion system comprising the lower base part 10 aligned to the upper base part 20 and coupled with the connector 30. The opening for connection tube 180 of the connector 30 is fluid communication with the lumen of the fluid connector tube 80, which can puncture through a membrane 50 on the upper base part 20 covering one of the openings on the upper base part. The fluid connector tube 80 connects to the cannula device 70, and the lumen of the fluid connector tube 80 is in fluid communication with the sealed chamber 200 of the cannula device 70. In some cases, a cannula of the cannula device 70 penetrates through the skin of a user of the infusion system, and the sealed chamber is in fluid communication through the cannula into the skin of the user. In some cases, the upper base part has a membrane 40 covering one of the openings 100 on the upper base part 20 for the cannula part 70. An o-ring 60 can help to secure the fluid seal of the cannula device 70 within the upper base part 20. The lower base part has an opening 110 for the cannula device. In cross-sectional view also shows the rotation guides 170 on the upper base part and locking protrusion 150 of the connector 30 that fits in the groove 140 of the lower base to limit movement of the infusion device.

Figure 6:
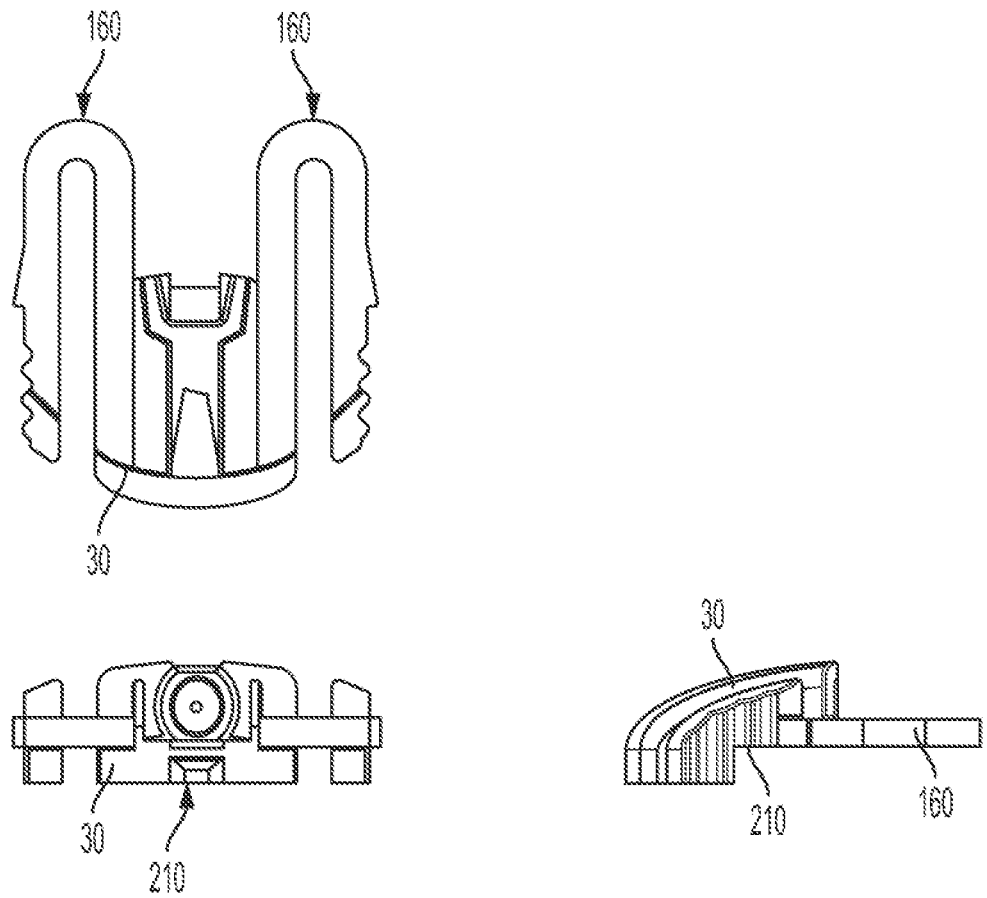
FIG. 6: Depicts a snap hook and connection included within upper base part 20.

FIG. 6 depicts details of the connector 30 having two snap hooks 160 on either side of the connector and a notch 210, which provides space for the connector 30 to be placed adjacent to the lower base part 10 when the connector is coupled to the base parts.

Figure 7:
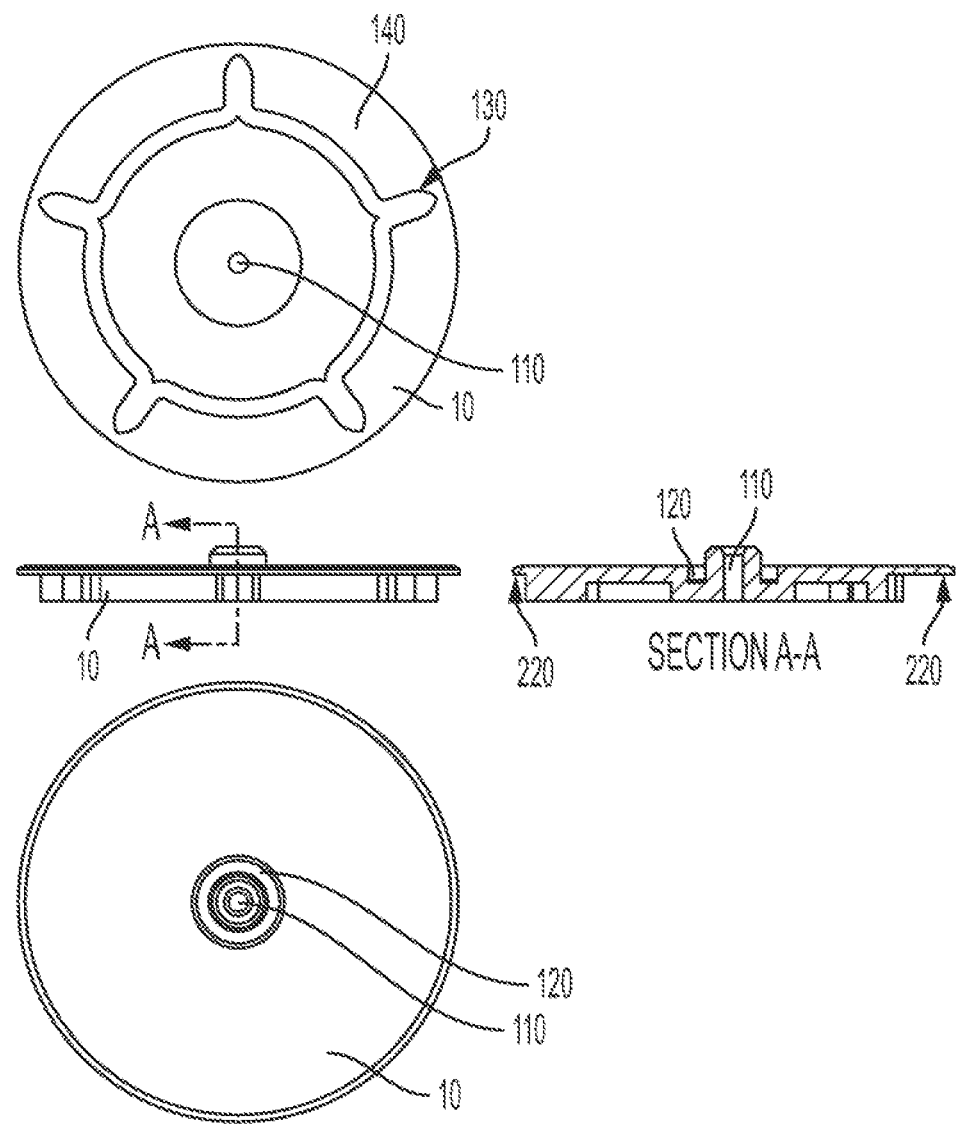
FIG. 7: Depicts guide to connection of upper base part and lower base part.

FIG. 7 depicts details of the lower base part 10. The lower base part 10 may have a plurality of grooves 140 in between a plurality of guiding protrusions 130. The grooves 140 and the guiding protrusions 130 are on the side of the lower base part 10 that adheres to the skin of the user of the device. A cross-sectional view of the lower base part 10 across section A-A shows the opening 110 for a cannula device 70 on the lower base part 10 and a rotation groove 120 at or near the center of the lower base part 10. The opening 110 provides a space in the lower base part for a catheter or a cannula of the cannula device to pass through. The rotation groove 120 may be concentric to the opening 110 or surround the opening 110 partially or fully. The rotation groove 120 provides a guide for a notched rotatable part of the upper base part 20 to fit into and rotate relative to the lower base part 10 within the rotation groove. The lower base part 10 also has recessed ends 220 at or near its perimeter that fit into the rotation guide of the upper base part to keep the upper base part connected to the lower base part.

Figure 8:
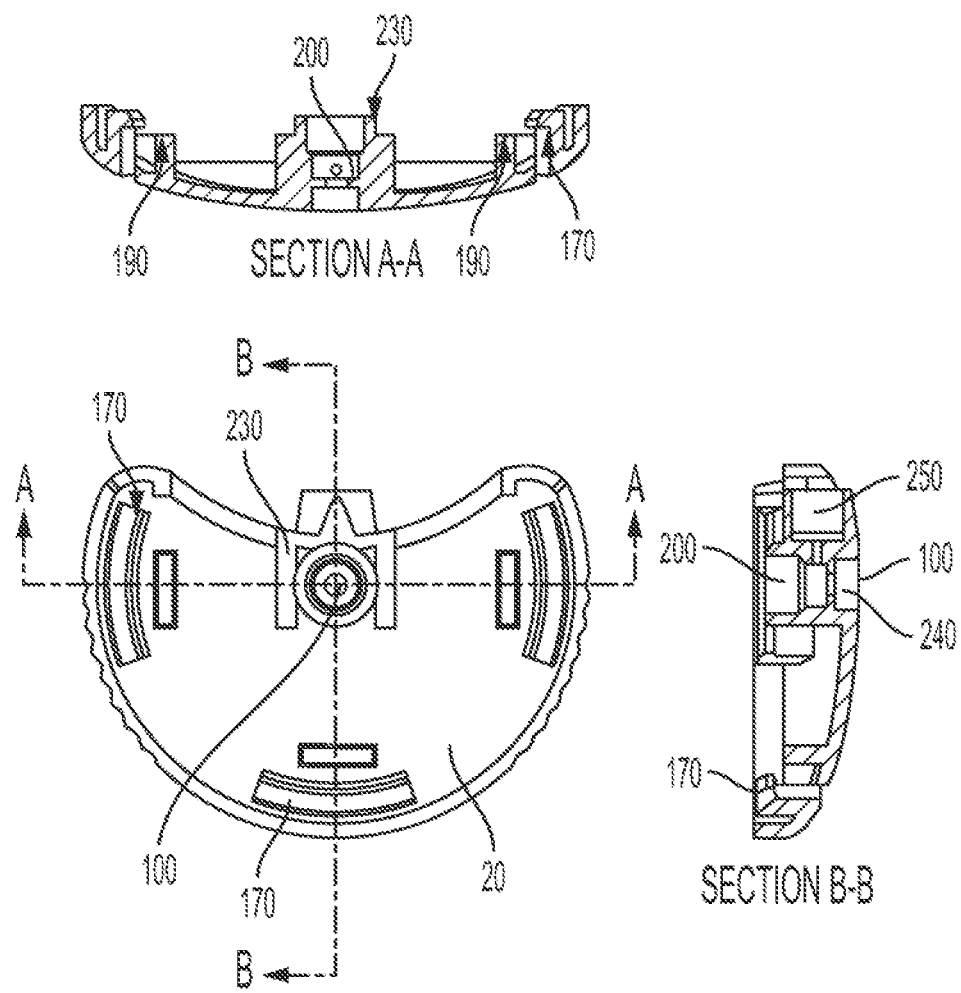
FIG. 8: Depicts alternate view of guide for connector part to connect lower base part and upper base part.

FIG. 8 depicts details of upper base part 20. The upper base part 20 has a plurality of rotation guides 170 that help to keep the upper base part 20 connected to the lower base part 10 and an opening 100 for a cannula device. A cross-sectional view of the upper base part 20 across section A-A shows that the rotation guides 170, the guides 190 for the connector to insert into, and a tapped rotatable part 230 that fits into the rotation groove 120 on the lower base part 10. The A-A cross section also shows a seal chamber 200 that can be in fluid connection with the lumen of the fluid connector tube 80 and connection tube 90 of the connector 30 and to a reservoir of a drug. A cross-sectional view of the upper base part 20 across section B-B shows an alternate view of the sealed chamber 200, rotation guides 170, an opening 100 for a cannula device, along with a space 240 at the top of the upper base part 20 for a membrane 40 and a space 250 on the side of the upper base part 20 for a membrane 50 that can be penetrated by the fluid connector tube 80 of the connector 30.

Figure 9:
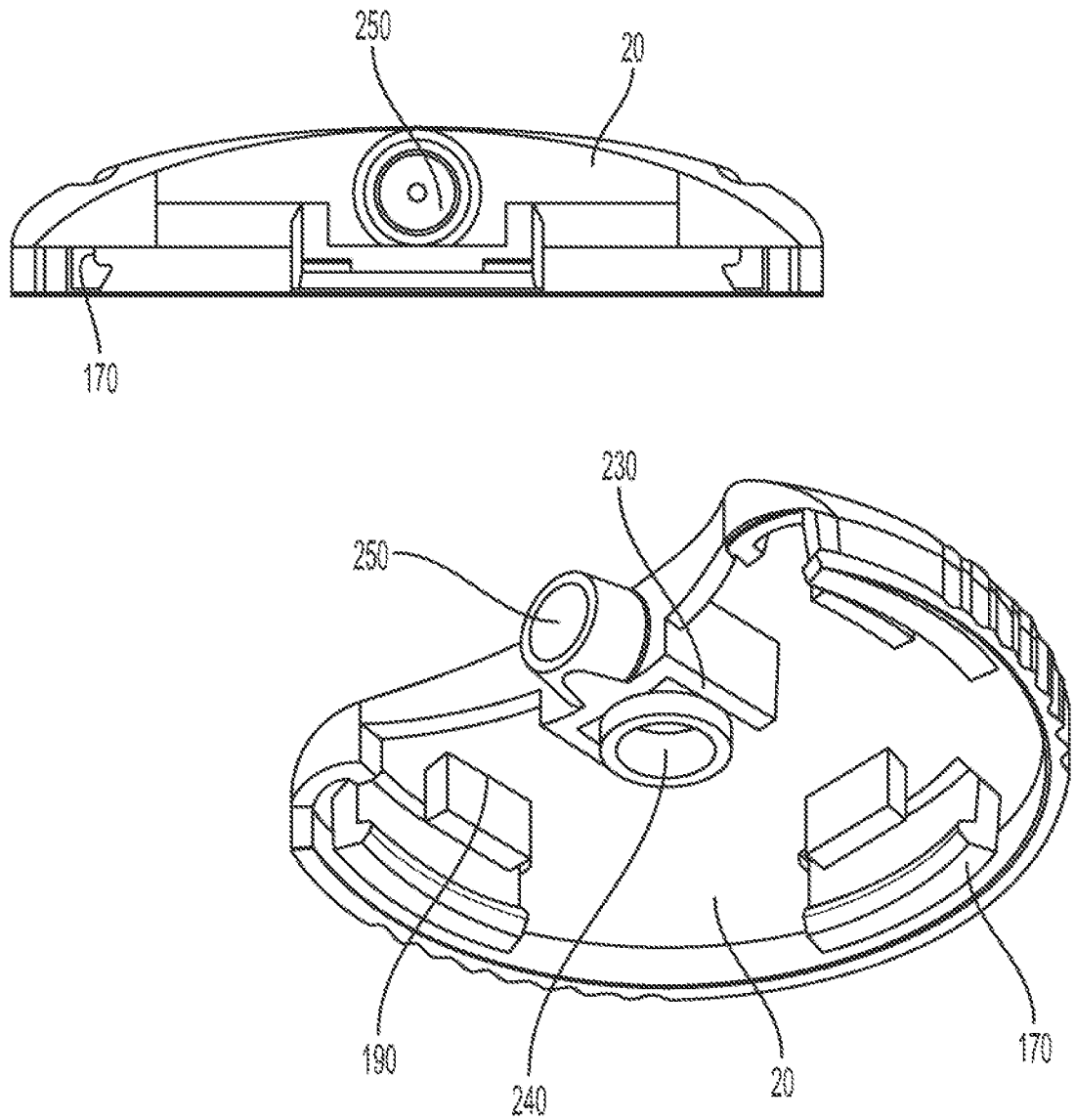
FIG. 9: Depicts bottom and side view of upper base part 20.

FIG. 9 depicts further views of the upper base part 20. The side profile view of the upper base part 20 shows the rotation guides 170 and a space 250 on the side of the upper base part 20 for a membrane 50. The view from underneath of the upper base part 20 shows the rotation guides 170, the guides 190 for the connector to insert into, the tapped rotatable part 230 that fits into the rotation groove 120 on the lower base part 10 and spaces 240 and 250 for membranes 40 and 50, respectively.

Figure 10:
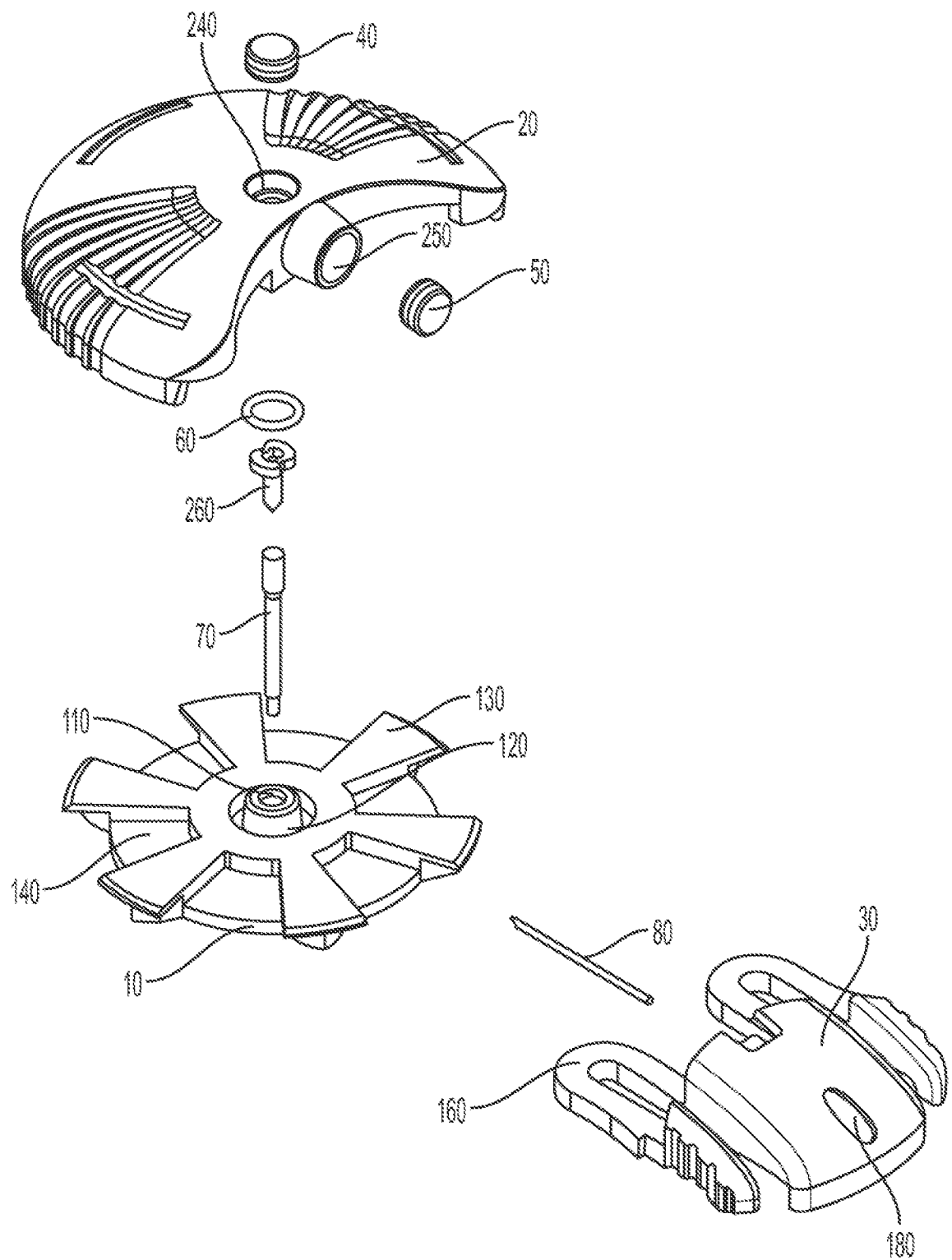
FIG. 10: Exploded view of upper base part 20, lower base part 10 and connector part 30.

FIG. 10 depicts a second embodiment of the infusion systems disclosed herein. Lower base part 10 aligns with upper base part 20 through rotation groove 120 and an opening 110 through which a cannula device 70 passes through upper base part 20 and lower base part 10 and inserts into patient. The upper base part 20 has a space 240 for membrane 40 on top and a space 250 for membrane 50 on its side. The lower base part 10 has a number of grooves 140 in between the guiding protrusions 130 on the top side, or the same side as the rotation groove 120, of the lower base part 10. The upper base part 20 and the lower base part 10 house a cannula device 70 held in place by a cannula holder 260 through the openings 110, 240 at or near the center of the base parts. An o-ring may be placed in between the membrane 40 and top of the cannula housing 260 to provide a secure fluid seal in the base part. The base parts are coupled to the connector 30, where the snap hooks 160 fits into the upper base part 20 and the fluid connector tube 80 penetrates through membrane 50 to fluidly connect to the cannula device 70. The connector 30 has an opening 180 for connection tube to fluidly connect a reservoir of a medicament to the fluid connector tube 80 and the cannula device 70.

Figure 11A:
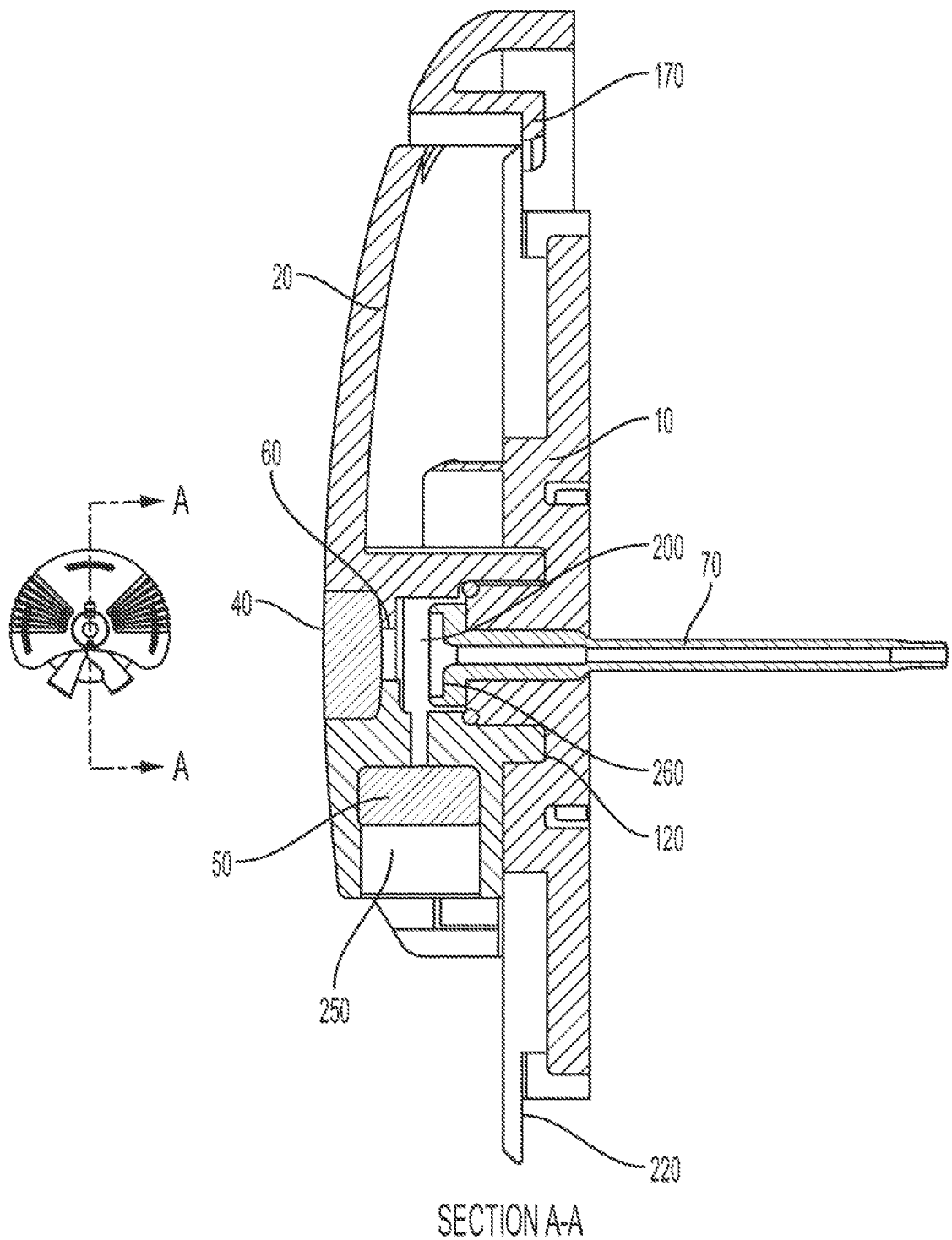
FIGS. 11A and 11B: Detail of upper base part 20 and lower base part 10 with cannula needle.
Figure 11B:
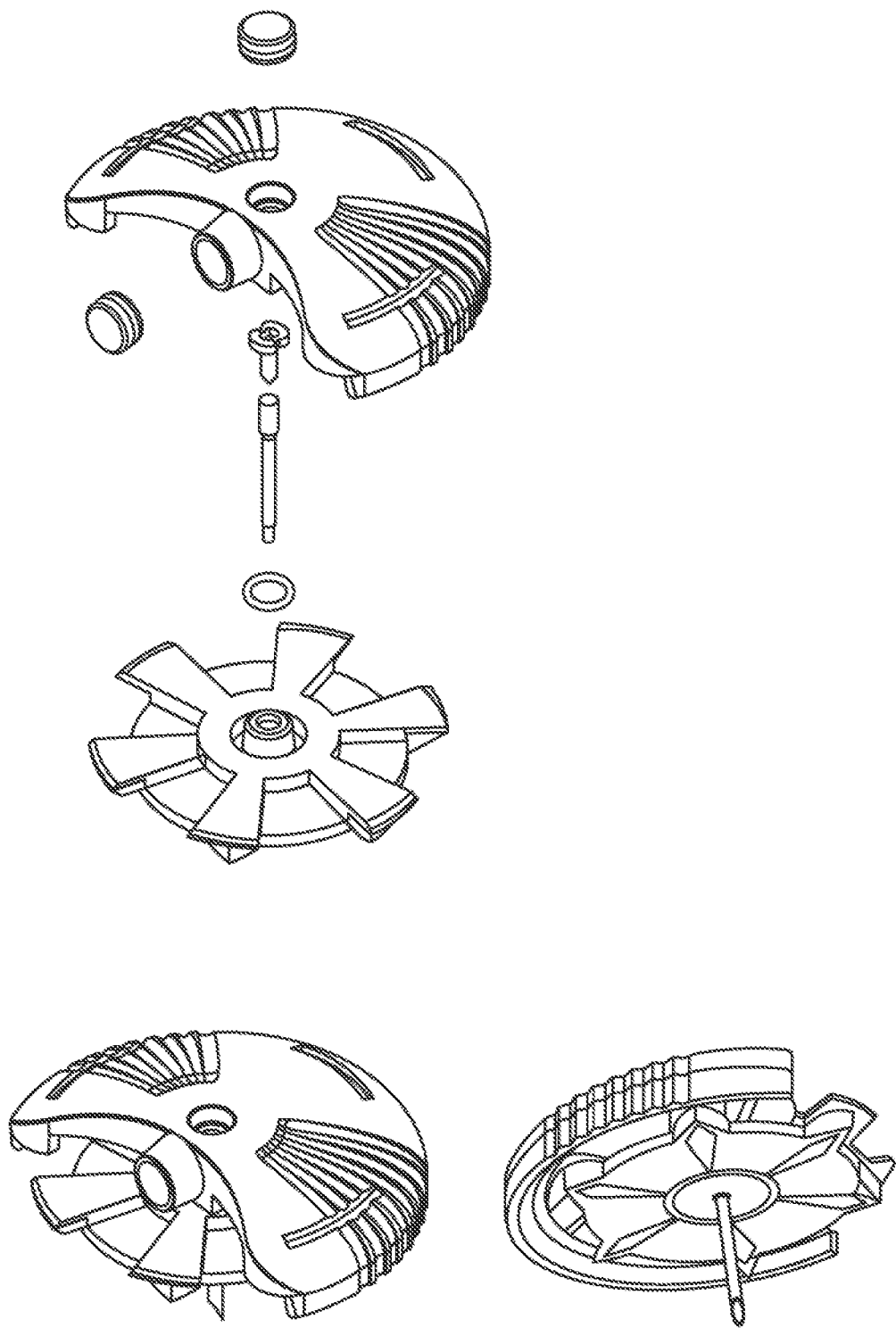

FIG. 11 depicts details of assembled upper base part 20 and lower base part 10 with cannula needle. The cross-sectional view across section A-A of the assembled upper base part 20 and lower base part 10 with a cannula device 70 shows a sealed chamber 200 in fluid communication with the cannula device 70 held in place in the base parts by the cannula housing 260. The fluid seal is secured by the o-ring 60, membrane 40, and membrane 50 in space 250 that can couple to a connector 30. The lower base part has recessed ends 220 that couples to the rotation guides 170 of the upper base part 20 to keep the upper and lower base parts together. The tapped rotatable part 230 on the upper base part 20 fits into the rotation groove 120 on the lower base part 10 to allow the upper base part 20 to rotate relative to the lower base part 10. An exploded view of the assembly and alternate assembled views are also shown.

Figure 12:
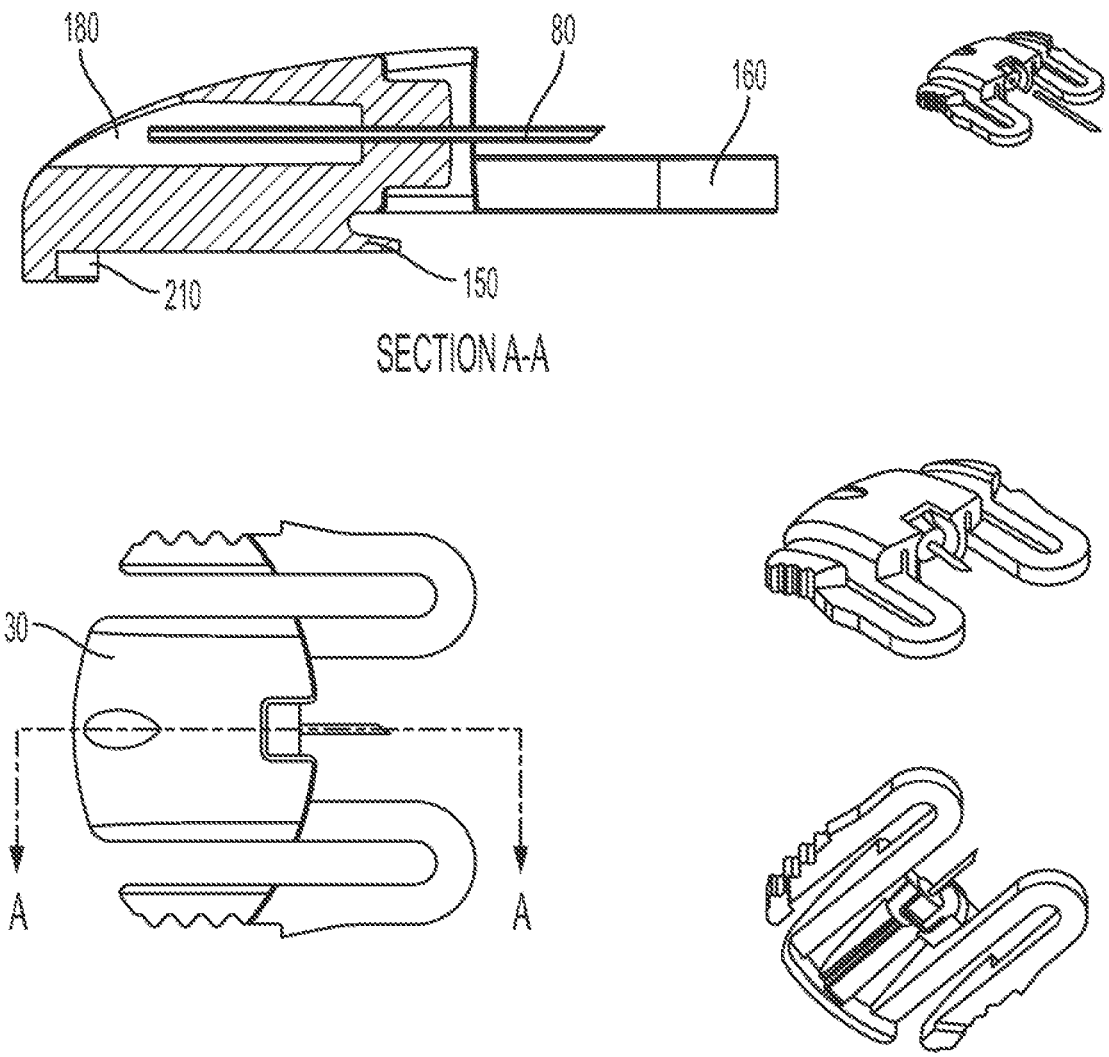
FIG. 12: Details of connector part 30.

FIG. 12 depicts details of connector part 30. The cross-sectional view of section A-A of the connector part 30 shows snap hook 160, a notch 210, which provides space for the connector 30 to be placed adjacent to the lower base part 10 when the connector is coupled to the base parts, an opening 180 for connection tube, and a fluid connector tube 80 that can penetrate membrane 50 in the upper base part to establish a fluid connection to the sealed chamber in the upper base part 20. An exploded view and alternate views of the connector are also shown.

Figure 13:
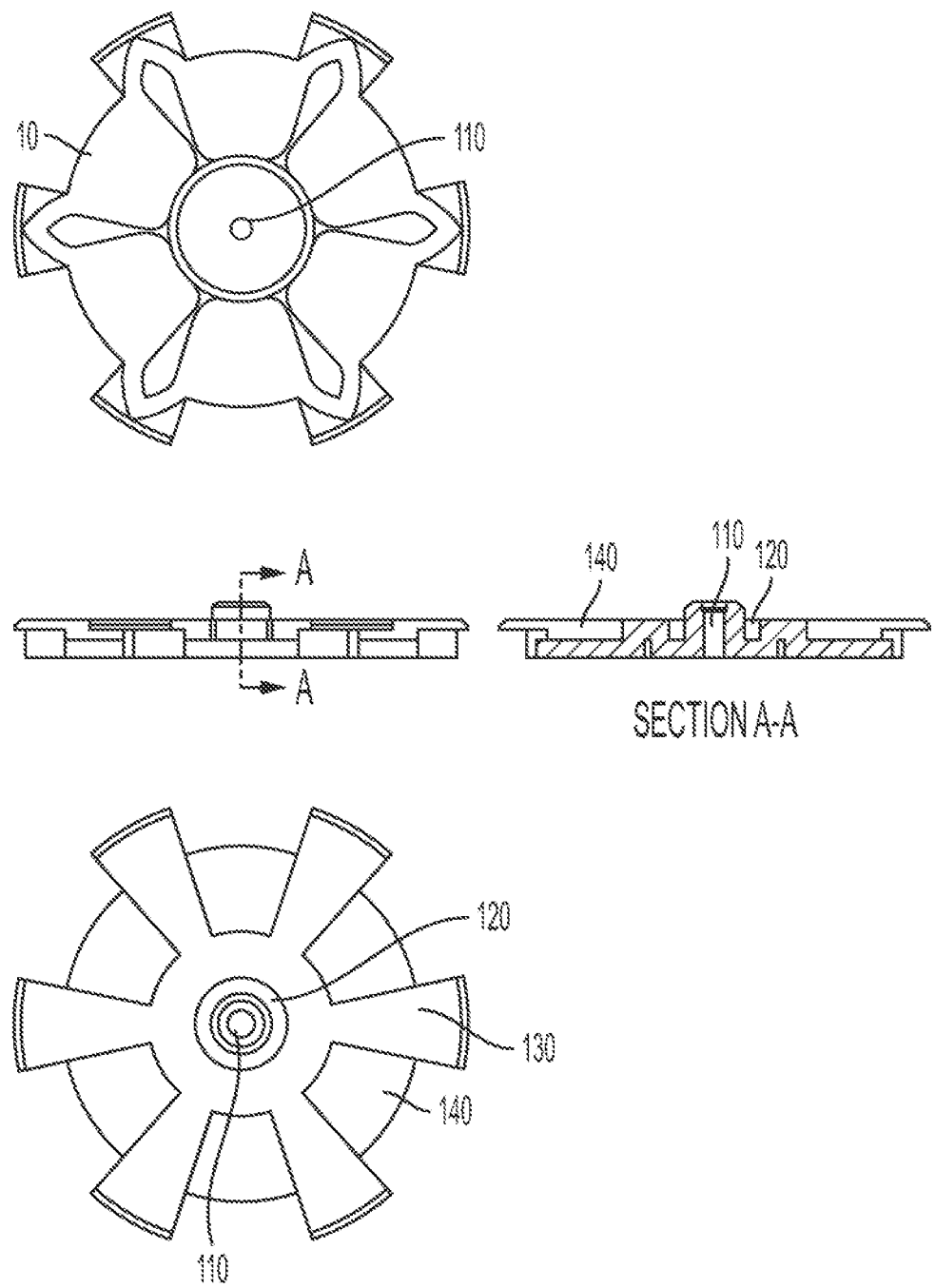
FIG. 13: Alternative embodiments and views of lower base part.

FIG. 13 depicts alternative embodiments and views of lower base part 10. The view from underneath the lower base part 10 shows the opening 110 for cannula device. The side view and cross-sectional view of section A-A shows the opening 110 for cannula device, rotation groove 120 surrounding the opening 110, and the groove 140 on the perimeter that couples to the locking protrusion on the connector to secure the coupling between the connector and the base parts. The view from the top of the lower base part 10 shows opening 110 for cannula device, rotation groove 120 surrounding the opening 110, a plurality of guiding protrusion parts 130, and grooves 140 on the perimeter in between the protrusion parts.

Figure 14:
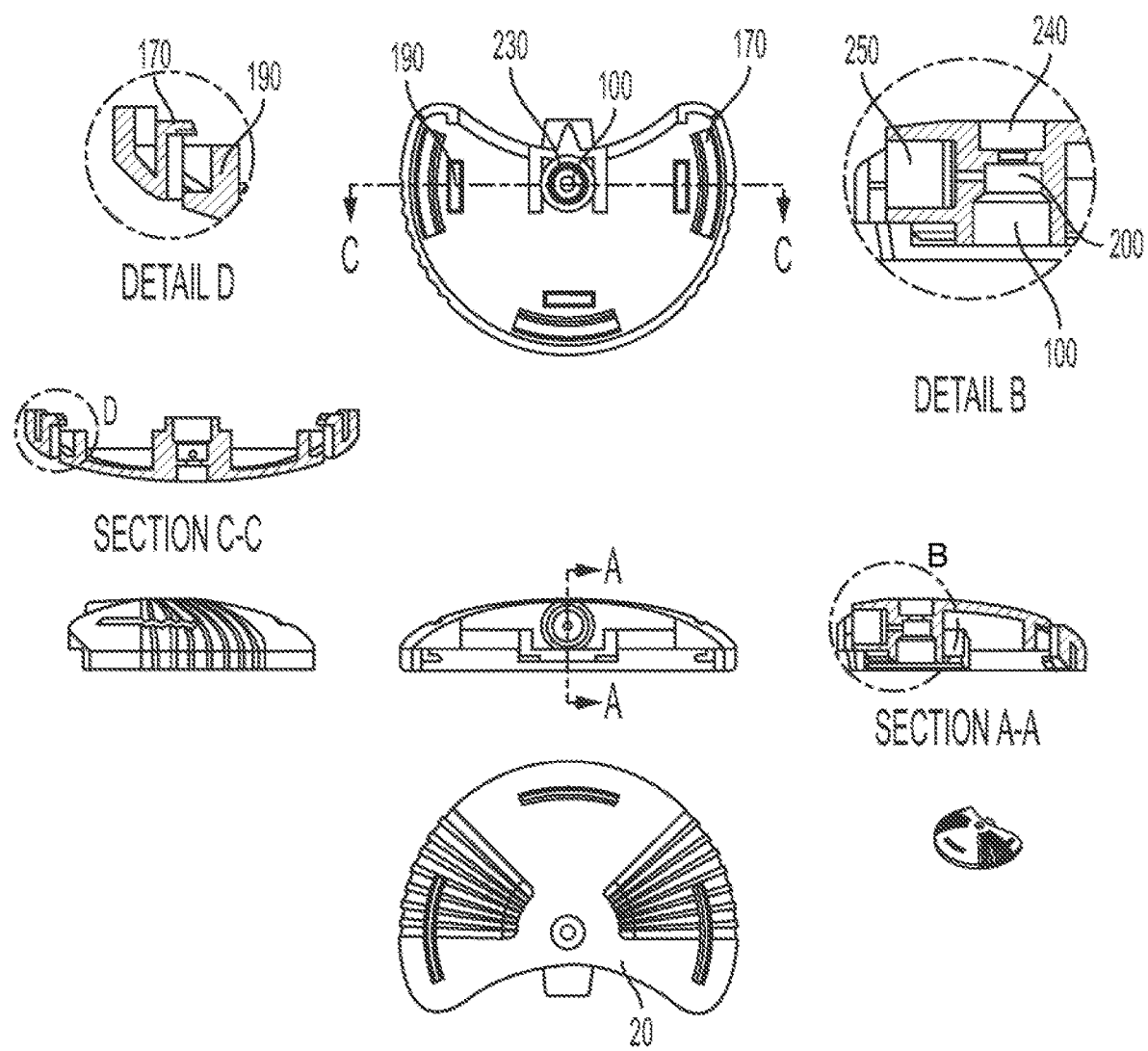
FIG. 14: Alternative embodiments and views of upper base part.

FIG. 14 depicts alternative embodiments and views of upper base part 20. The cross-sectional view of section A-A and the detailed view B show the sealed chamber 200 connected to the opening 100 for the cannula device and spaces 240, 250 that can be sealed with membranes 40, 50 to provide a fluid seal to the sealed chamber 200. The view from underneath the upper base part 20 shows the a plurality of rotation guides 170 that help to keep the upper base part 20 connected to the lower base part 10, the guides 190 for the connector to insert into, a tapped rotatable part 230 that fits into the rotation groove 120 on the lower base part 10, and an opening 100 for a cannula device. The cross-sectional view from section C-C and detailed view D show the rotation guides 170 protruding inwards on the underside of the upper base part 20 near its perimeter and the guides 190 that are interior to the rotation guides, which provides a space in between the rotation guides and the guides for the snap hooks of the connector to fit into.

Figure 15:
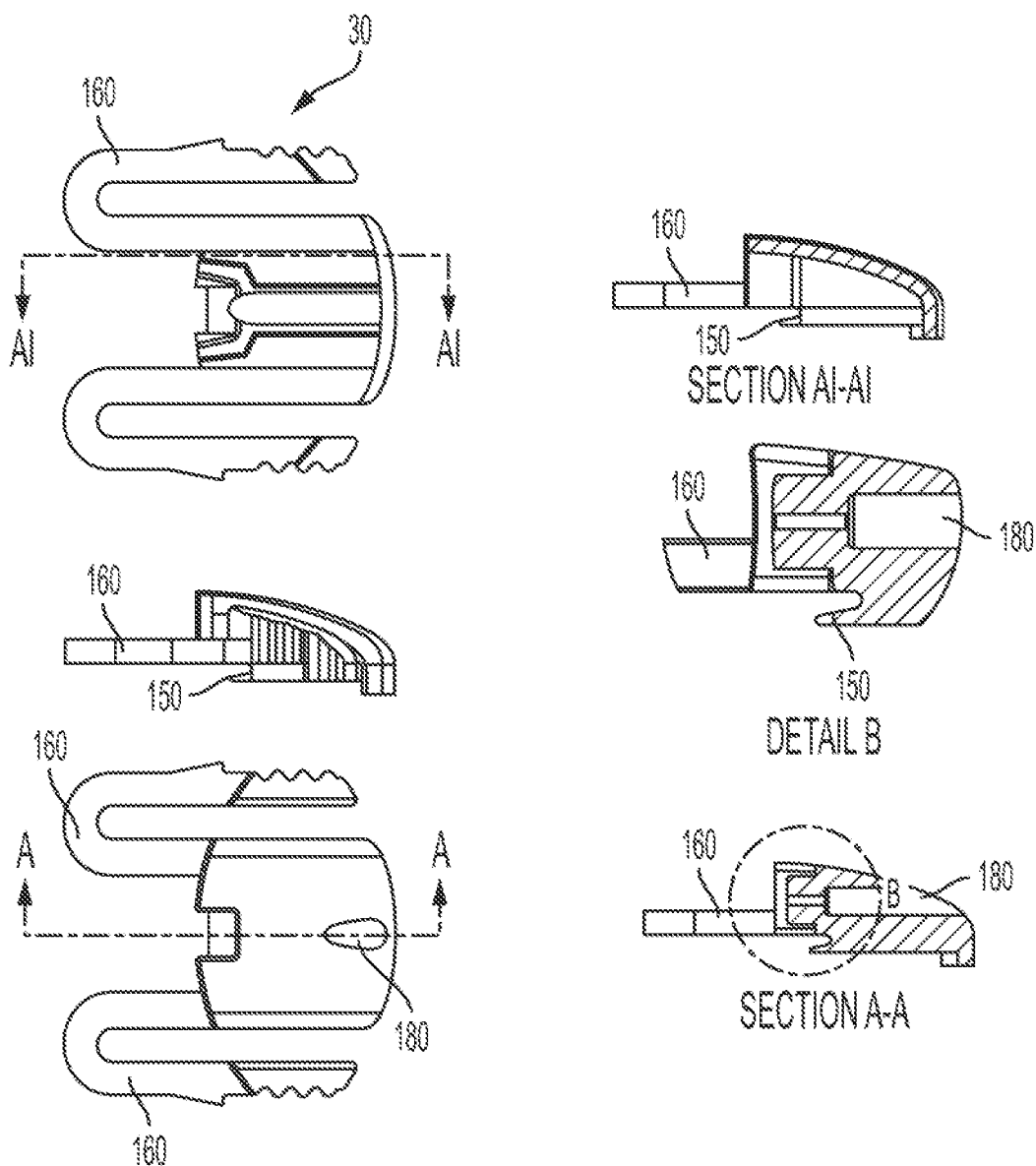
FIG. 15: Alternative embodiments and views of connector part.

FIG. 15 shows alternative embodiments and views of connector part 30. The connector part 30 has an opening 180 for connection tube and two snap hooks 160. The cross-sectional view of section AI-AI offset from the center shows a snap hook 160 extending out from the body of connector 30 and a locking protrusion 150 underneath the snap hook 160. The cross-sectional view of section A-A and detailed view B show the snap hook 160 and an opening 180 for connection tube in connection with the space for fluid connector tube and a locking protrusion 150 on the side of the connector that couples to the lower base part 10.

Figure 16:
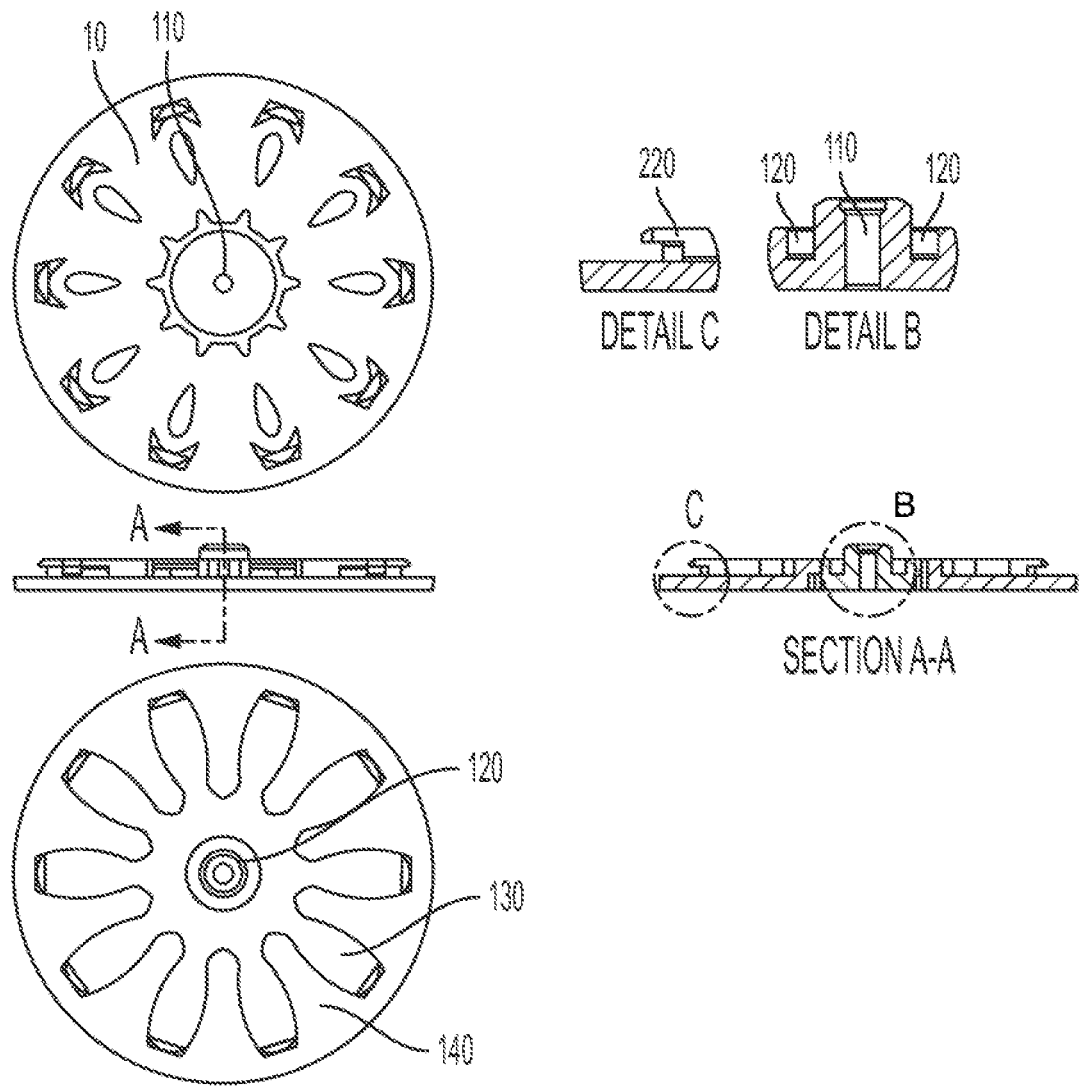
FIG. 16: Alternative embodiments and views of lower base part.

FIG. 16 illustrates alternative embodiments and views of lower base part 10. The lower base part 10 may have a number and/or dimensions of guiding protrusion parts 130 such that the size of the grooves 140 offers enough space for a locking protrusion 150 on the connector to fit into the groove with little to no extra space in the groove. A portion of the locking protrusion 150 may come into contact with a portion of the adjacent guiding protrusions 130. The lower base part may be designed to have the grooves 140 that offer little to no room for the lower base part to move or rotate when the lower base part is coupled to the connector and the locking protrusion of the connector is placed into one of the grooves 140. The cross-sectional view of section A-A and the detailed view B and C show the rotation groove 120 surrounding the opening 110 for the cannula part and the recessed ends 220 that fit into the rotation guides 170 of the upper base part 20 to keep the upper and lower base parts together.

Figure 17:
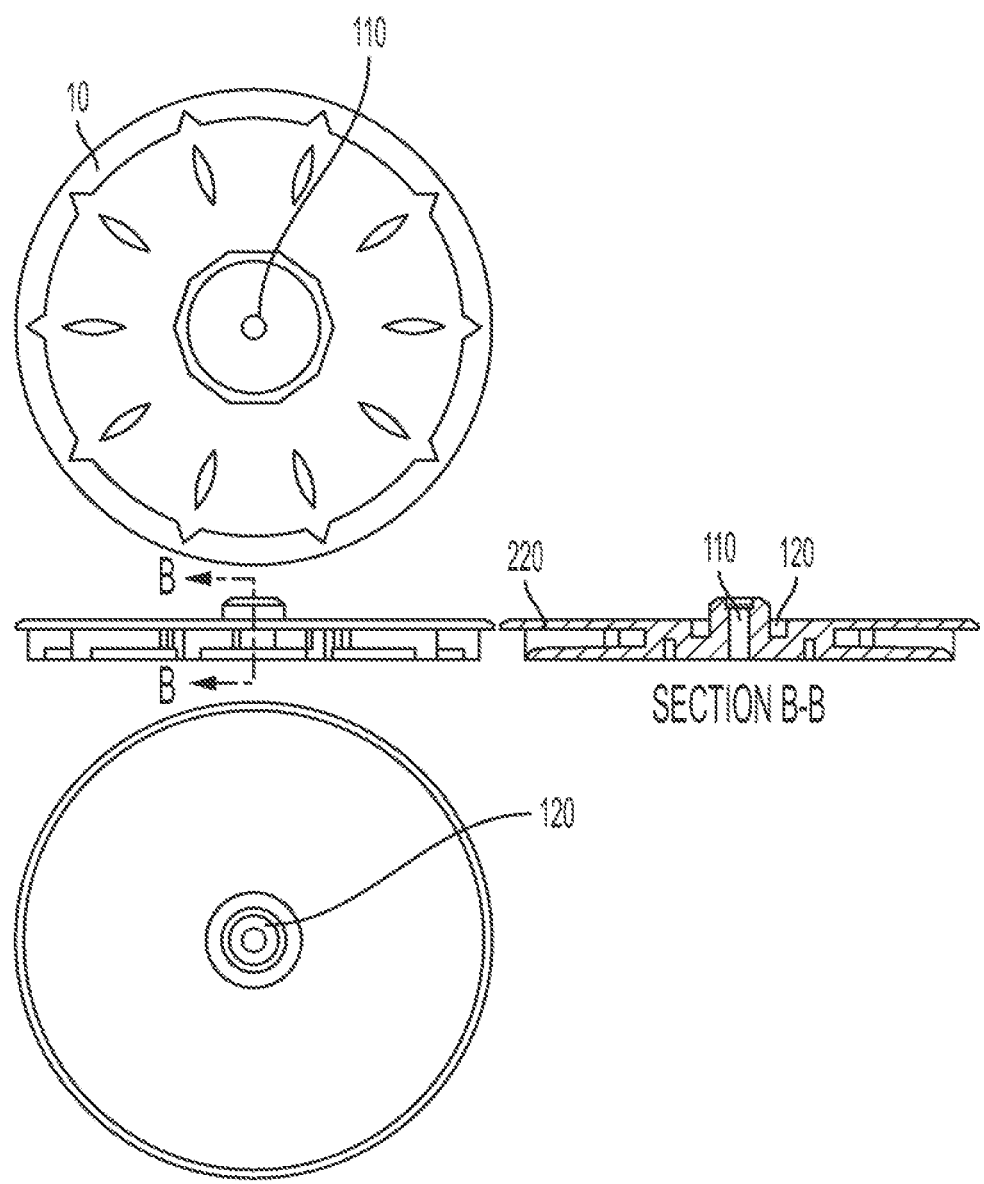
FIG. 17: Alternative embodiments and views of lower base part.

FIG. 17 shows alternative embodiments and views of lower base part 10. The cross-sectional view of section B-B shows the rotation groove 120 surrounding the opening 110 for the cannula part and the recessed ends 220 that fit into the rotation guides 170 of the upper base part 20 to keep the upper and lower base parts together.

Figure 18:
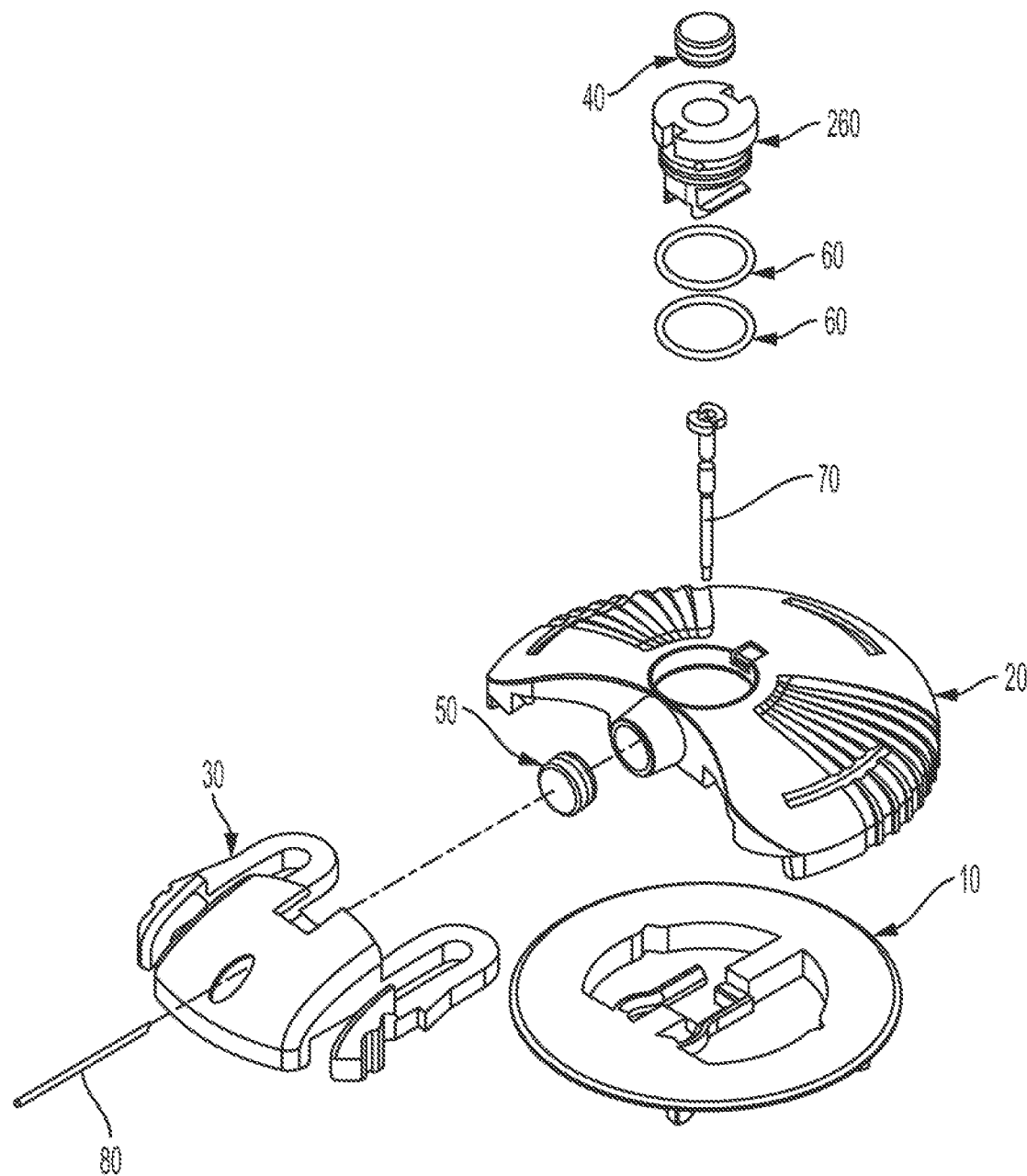
FIG. 18: Exploded view of an alternative embodiment of the infusion systems disclosed.

FIG. 18 shows exploded view of an alternative embodiment of the infusion systems disclosed. The cannula housing 260 can be inserted into an assembly of the upper base part 20 and the lower base part 10 through the opening 110 of the upper base part for the cannula device. The cannula housing 260 may be sealed at the top with a membrane 40 and hold the cannula device 70 to extend out from the lower portion of the cannula housing 260. The fluid seal between the wall of the opening 110 of the upper base part and the cannula housing 260 may be secured by at least one o-ring 60 or two o-rings as shown. A membrane 50 can provide a fluid seal to the sealed chamber within the upper base part 20, where the membrane can be penetrated by the fluid connector tube 80 when the connector 30 is coupled to the upper and the lower base parts 20, 10 and forms a fluid connection from the cannula device 70 through the sealed chamber in the upper base part to a reservoir connected to the fluid connector tube.

FIG. 19 shows alternative embodiment of the infusion systems disclosed, including a viewing hole for monitoring the skin condition of the patient. The viewing hole 270 on the lower base part 10 allows for viewing and monitoring of the condition of the skin underneath the infusion system once placed on the skin of a patient. In some cases, the viewing hole 270 may comprise a clear, transparent material. In some cases, the viewing hole 270 is left open and uncovered.

Figure 20:
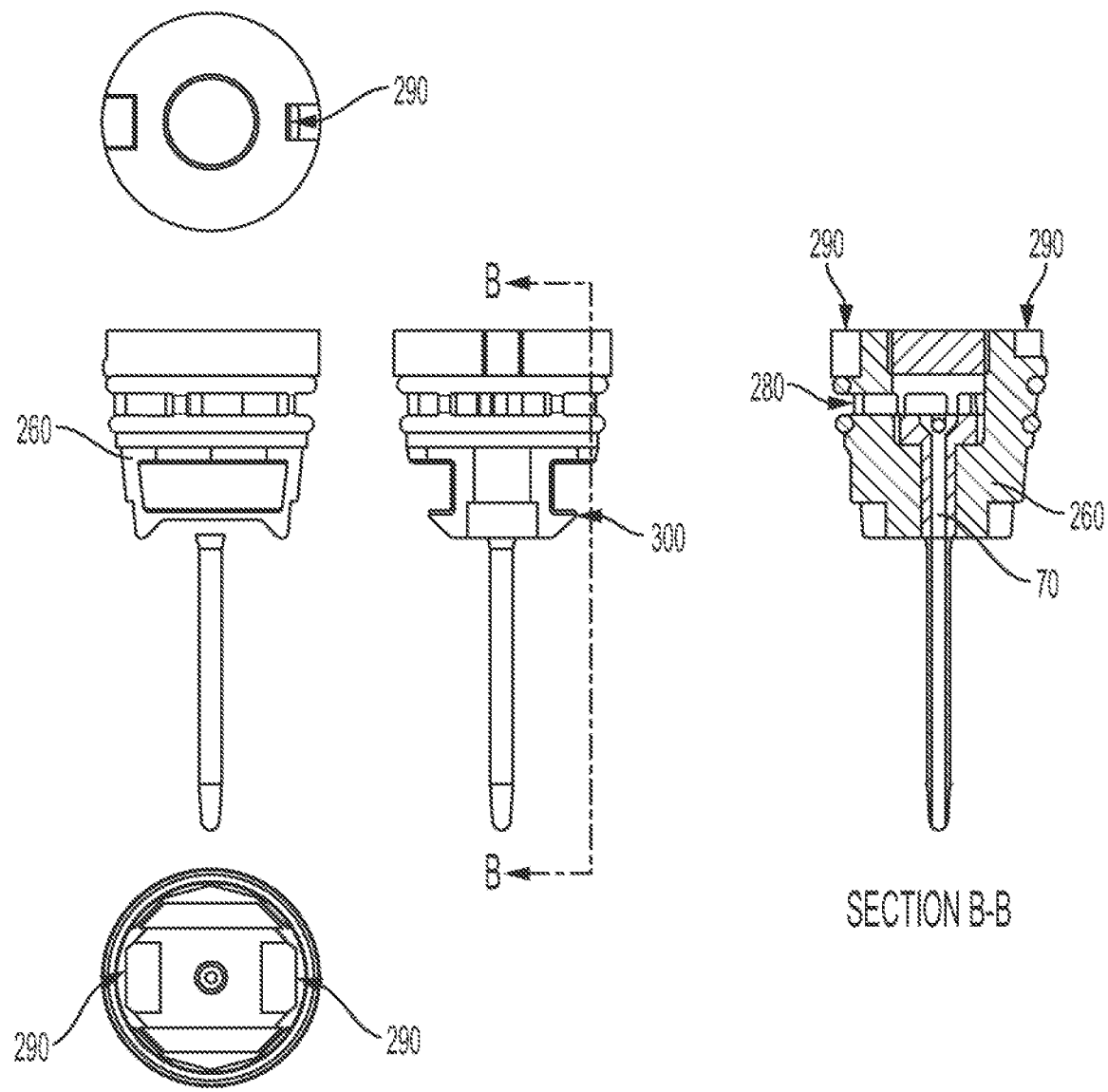
FIG. 20: Depicts cannula and space for cannula connection with connector part, and guides for insertion of the cannula with the infusion systems disclosed herein. The guides maintain position and orientation of the cannula when inserted.

FIG. 20 depicts cannula device 70 and cannula housing 260 and space 280 for cannula connection with connector part 30, and guides 290 for insertion of the cannula with the infusion systems disclosed herein. The guides 290 maintain position and orientation of the cannula device 70 when inserted. The guides 290 may be notches on the outer wall of the cannula housing 260 or the body portion of the cannula device 70 that a portion of the upper or lower base parts can fit into and secure the orientation of the cannula housing. The cross-sectional view of section B-B shows a space 280 for the fluid connector tube 80 fit into to establish a fluid connection to the sealed chamber and the cannula device. The cannula housing 260 or the cannula device 70 may have at least one fastener 300 to provide a surface for the cannula housing or the cannula to fit into the openings for the cannula device on the base parts.

Figure 21:
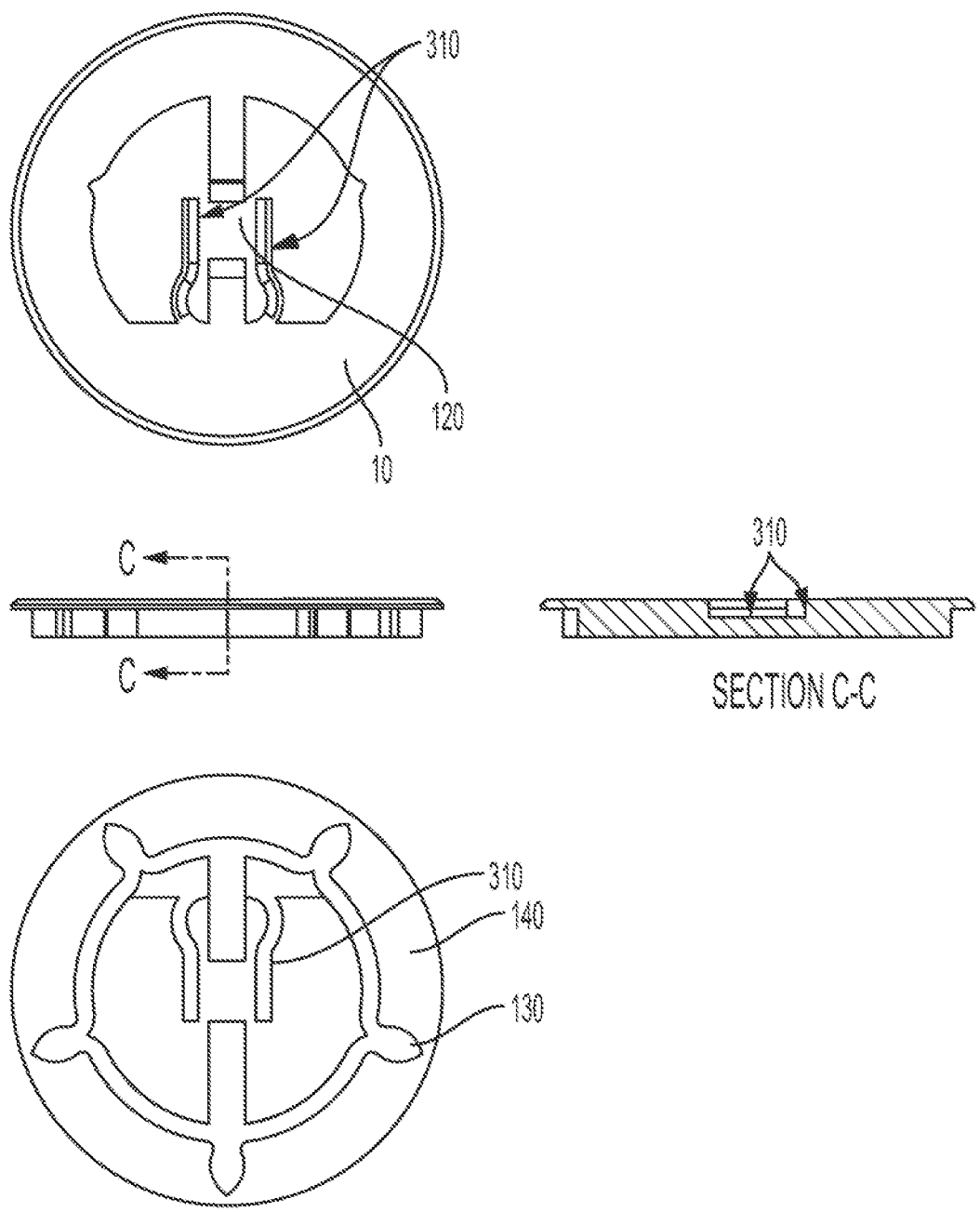
FIG. 21: Details of the guides including arms for retaining the cannula housing and guide for maintaining position and orientation of the cannula when inserted.

FIG. 21 shows details of the lower base part 10 including arms 310 for retaining the cannula device 70 or cannula housing 260. The arms 310 provide a guide for maintaining position and orientation of the cannula device 70 or the cannula housing 260 when inserted into the lower base part 10 and into the skin of the patient. The opening 120 on the lower base part 10 for the cannula device may be flanked by the arms 310 that retain the cannula device 70 or cannula housing 260 in place once inserted into the lower base part to be inserted into the skin of the patient. The lower base part 10 can have guiding protrusions 130 and grooves 140 in between the guiding protrusions around the arms 310. In some cases, the arms 310 are flexible and bend. In some cases, the arms 310 comprise flexible polymers or plastics. The cross-sectional view of section C-C shows the arms 310 in the lower base part 10.

Figure 22:
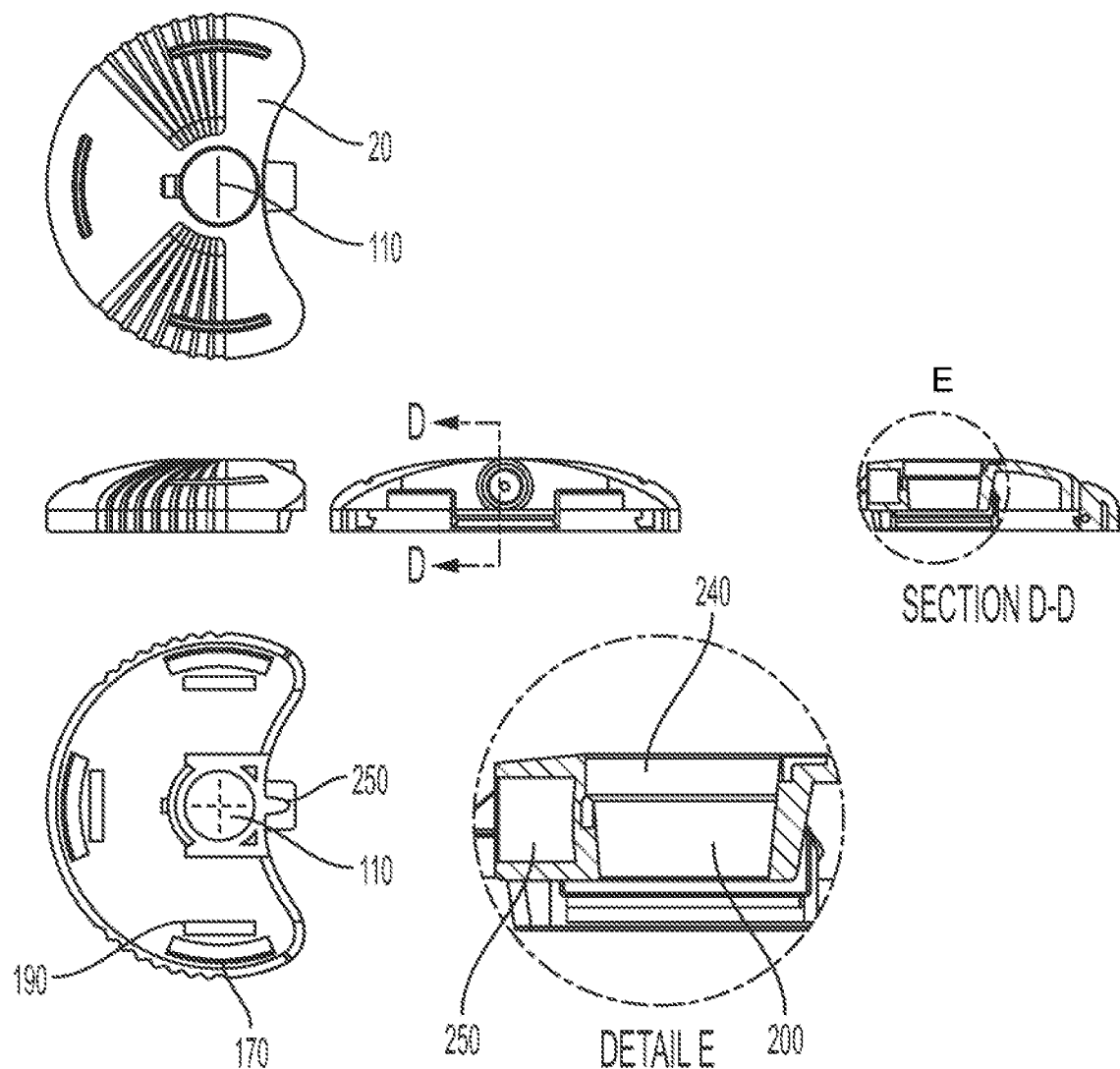
FIG. 22: Alternative embodiments and views of upper base part.

FIG. 22 shows alternative embodiments and views of upper base part 20. The upper base part 20 shown can accommodate a cannula housing 260 or a cannula device 70 that is inserted through an opening 110 of the upper base part as shown in FIG. 18. The upper base part 20 has opening 110 sized to accommodate a cannula housing 260 or a cannula device 70. The view from underneath the upper base part 20 shows the opening 110 connected to a space 250 for the membrane 50 and a plurality of rotation guides 170 near the perimeter of the upper base part 20 and guides 190 for connector to fit the upper base part. The cross-sectional view of section D-D and the detailed view of E show the sealed chamber 200 in connection with the spaces 240, 250 for membranes 40, 50, respectively, that can form a sealed chamber once the membranes 40, 50 seal the spaces 240, 250.

Figure 23:
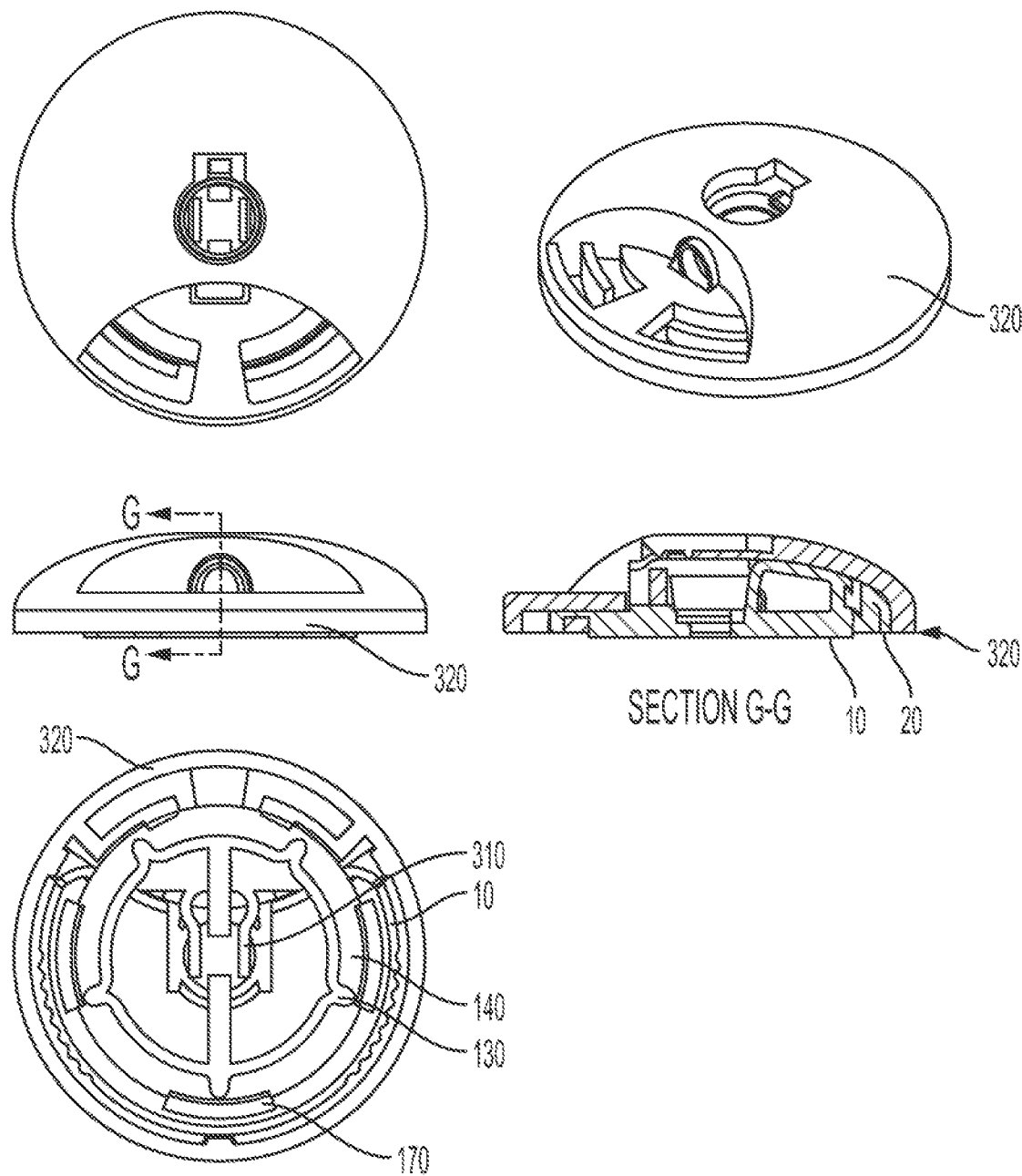
FIG. 23: Alternative embodiments and views of lower base part, upper base part and alignment shell.

FIG. 23 shows alternative embodiments and views of lower base part 10, upper base part 20, and alignment shell 320. The alignment shell 320 is placed over the upper base part 20 and helps to align the upper base part 20 and the lower base part 10. The alignment of the base parts helps to ensure the sealed chamber 200 has a good fluid seal and the fluid connection from the fluid connector tube of the connector through the sealed chamber and the cannula device is sealed and maintained. The view from underneath the assembly of the alignment shell 320, upper base part 20, and the lower base part 10 shows that the arms 310 at the opening to receive the cannula device or the cannula housing, along with the guiding protrusion parts 130 and the grooves 140 in between the guiding protrusion parts, and the rotation guides 170 from the upper base part 20 securing the connection to the lower base part 10.

Figure 24:
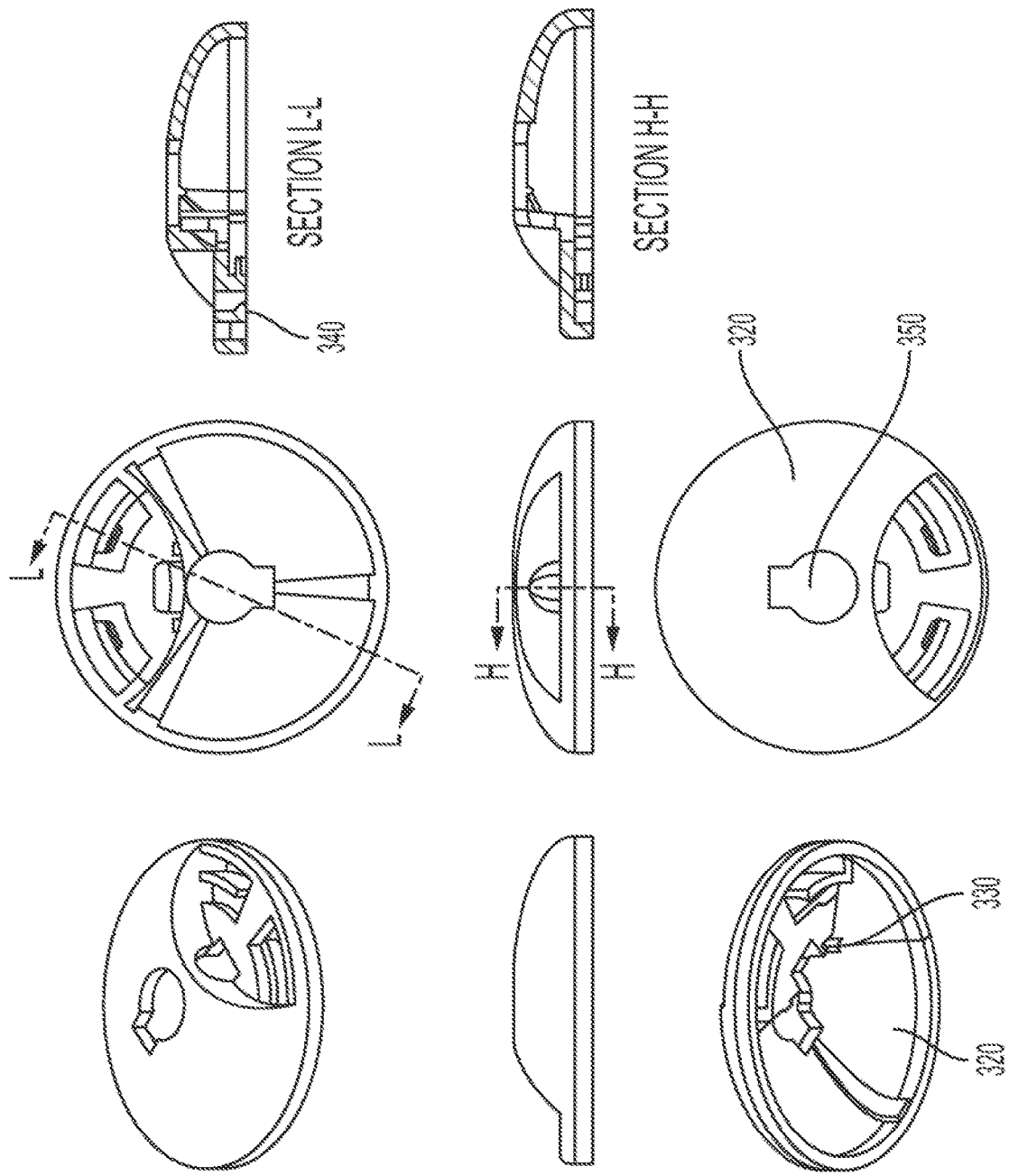
FIG. 24: Details of alternative embodiments of alignment shell having alignment pegs on and securing tabs.

FIG. 24 depicts details of an embodiment of an alignment shell 320, including alignment pegs 330 and securing tabs 340 on alignment shell. The alignment pegs 330 are protrusions or pegs on the inner surface of the alignment shell and fits into a recessed portion of the upper base part 20. 320. The alignment pegs 330 helps to align the alignment shell 320 with the upper base part 20. The securing tabs 340 secure the alignment shell 320 the lower base part 10 by fitting into a recessed portion of the lower base part 10.

FIG. 25 shows alternative embodiments and views of upper base part 20 and lower base part 10 with cannula device 70. In some instances, the cannula device is placed off the center of the upper and lower base parts. The lower base part 10 may not need an opening 110 for the cannula device when the lower base part is smaller than the upper base part 20 and the cannula device is inserted through the upper base part in the space between the upper base part and the lower base part. The cannula devices that are placed off center can be placed after the upper base part and lower base part have been rotated and secured to the desired position.

Figure 26:
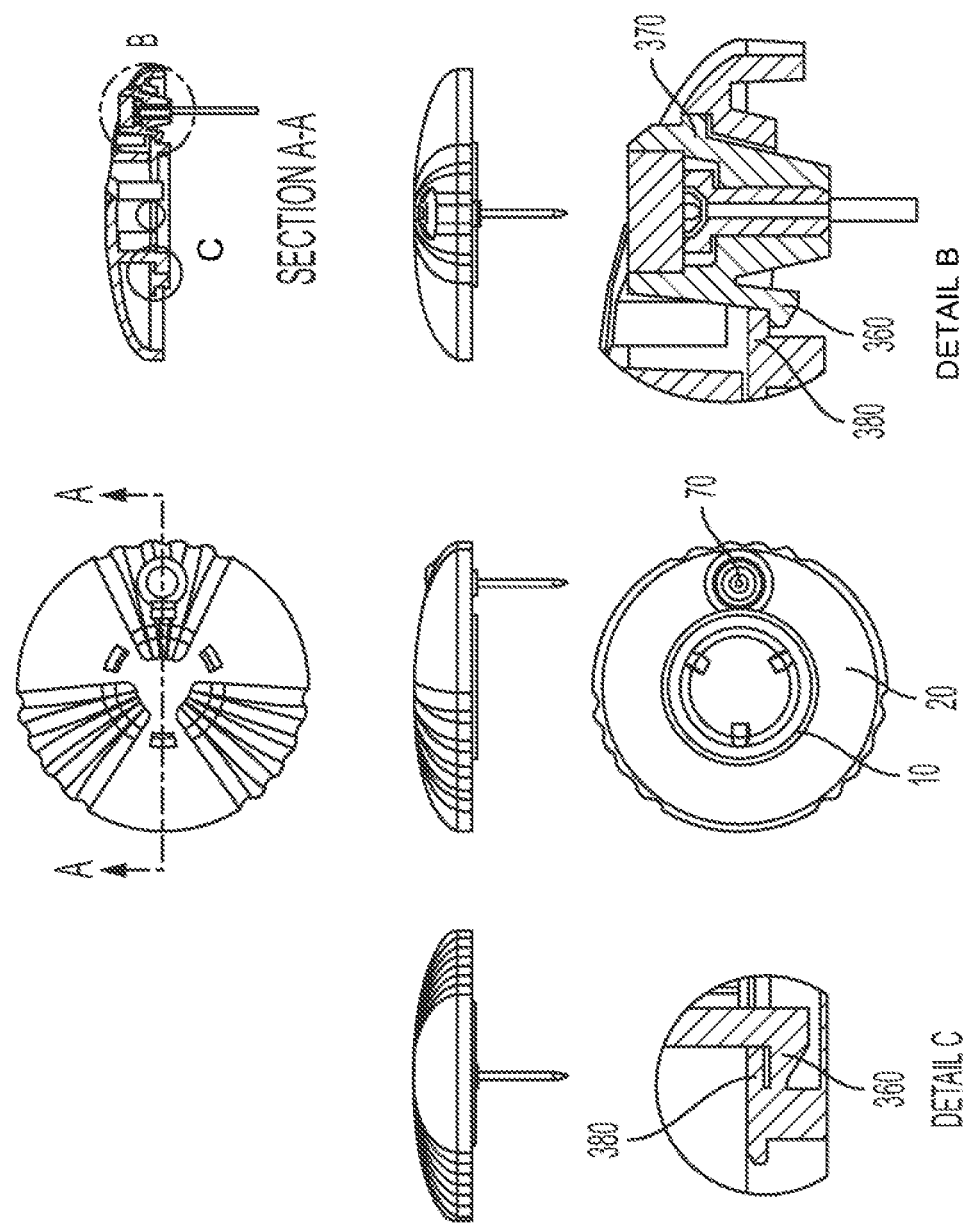
FIG. 26: Alternative embodiments and views of upper base part and lower base part with cannula.

FIG. 26 shows detailed views of upper base part 20 and lower base part 10 with cannula device 70 and a cannula housing 260 that are placed off center of the base parts. The cannula housing 260 can have a tab 360 that latches to the a protrusion part 380 on the upper base part 20 and a protrusion part 370 on the cannula housing that fit into a recessed groove on the upper base part to secure the cannula housing 260 into the upper base part 20. The details are shown in cross-section A-A and detailed views B and C.

Figure 27:
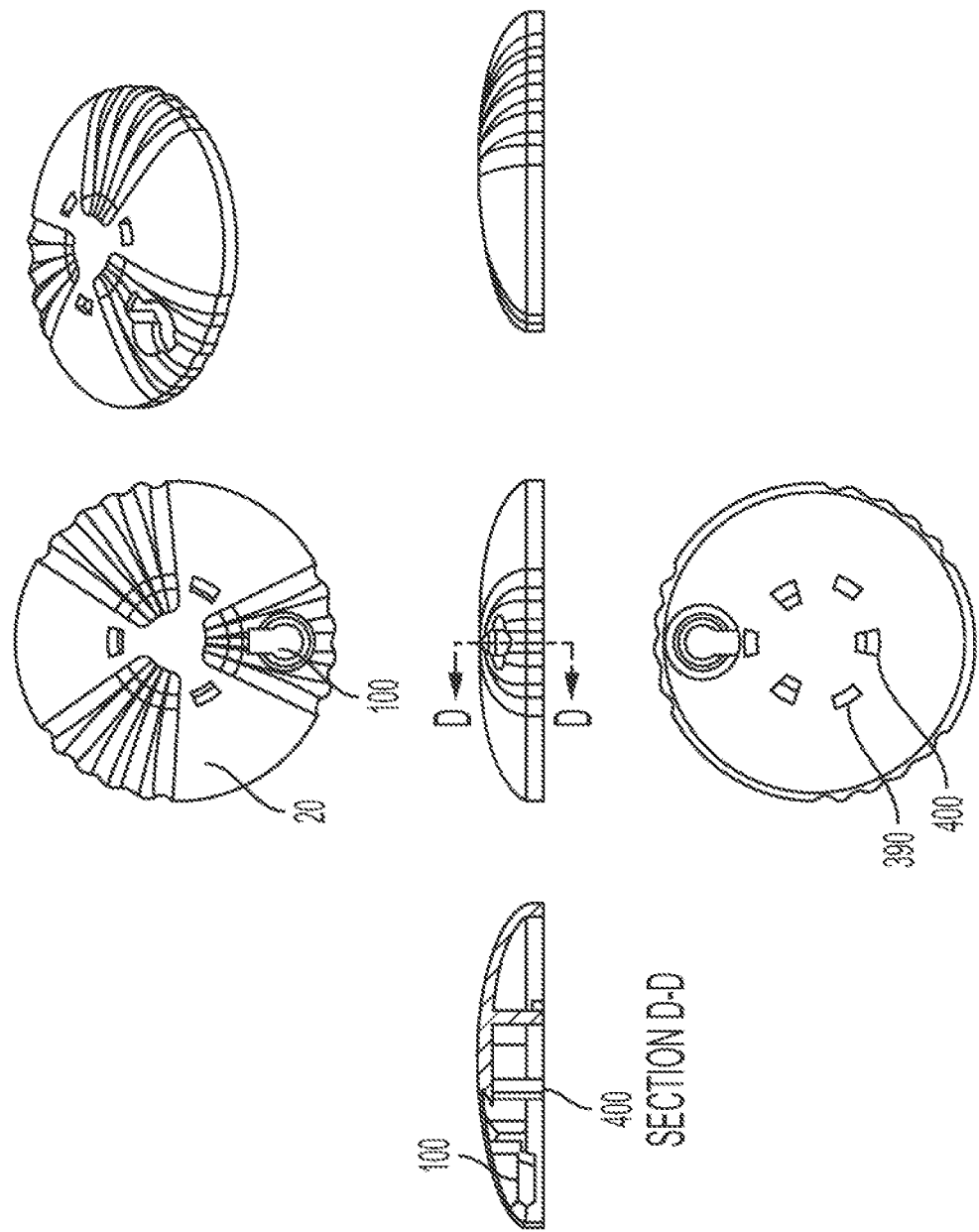
FIG. 27: Alternative embodiments and views of upper base part.

FIG. 27 shows alternative embodiments and views of upper base part 20. In some instances, the upper base part 20 has opening 100 for the cannula device that is off center, where the opening has a recessed portion and a protrusion part to fit with the cannula housing. The upper base part 20 has a plurality of holes 390 alternated with inner surface tabs 400 on the inner surface of the upper base part 20 to secure the connection to the lower base part 10.

Figure 28:
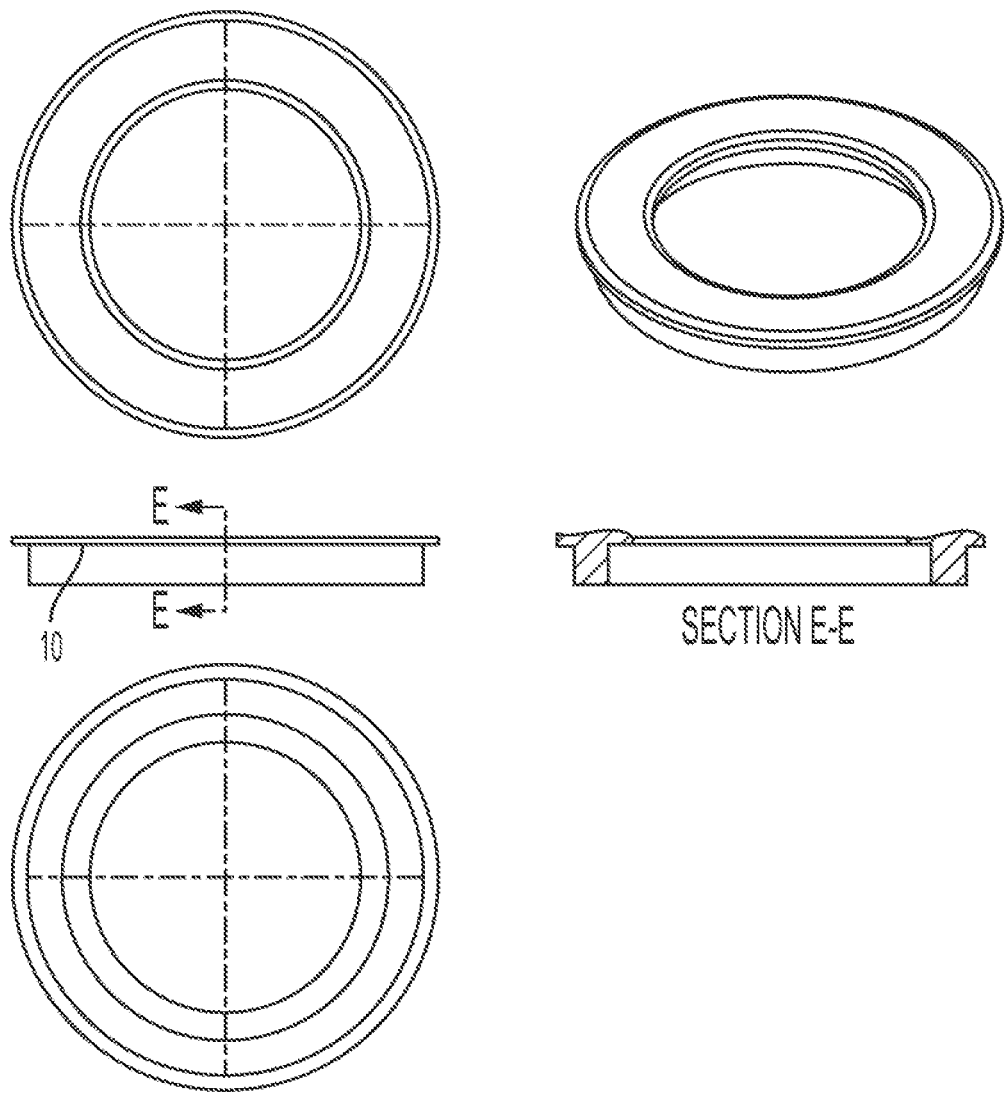
FIG. 28: Depicts lower base part.

FIG. 28 depicts an embodiment of a lower base part 10 that fits with an upper base part 20 having an off center opening for a cannula device.

Figure 29:
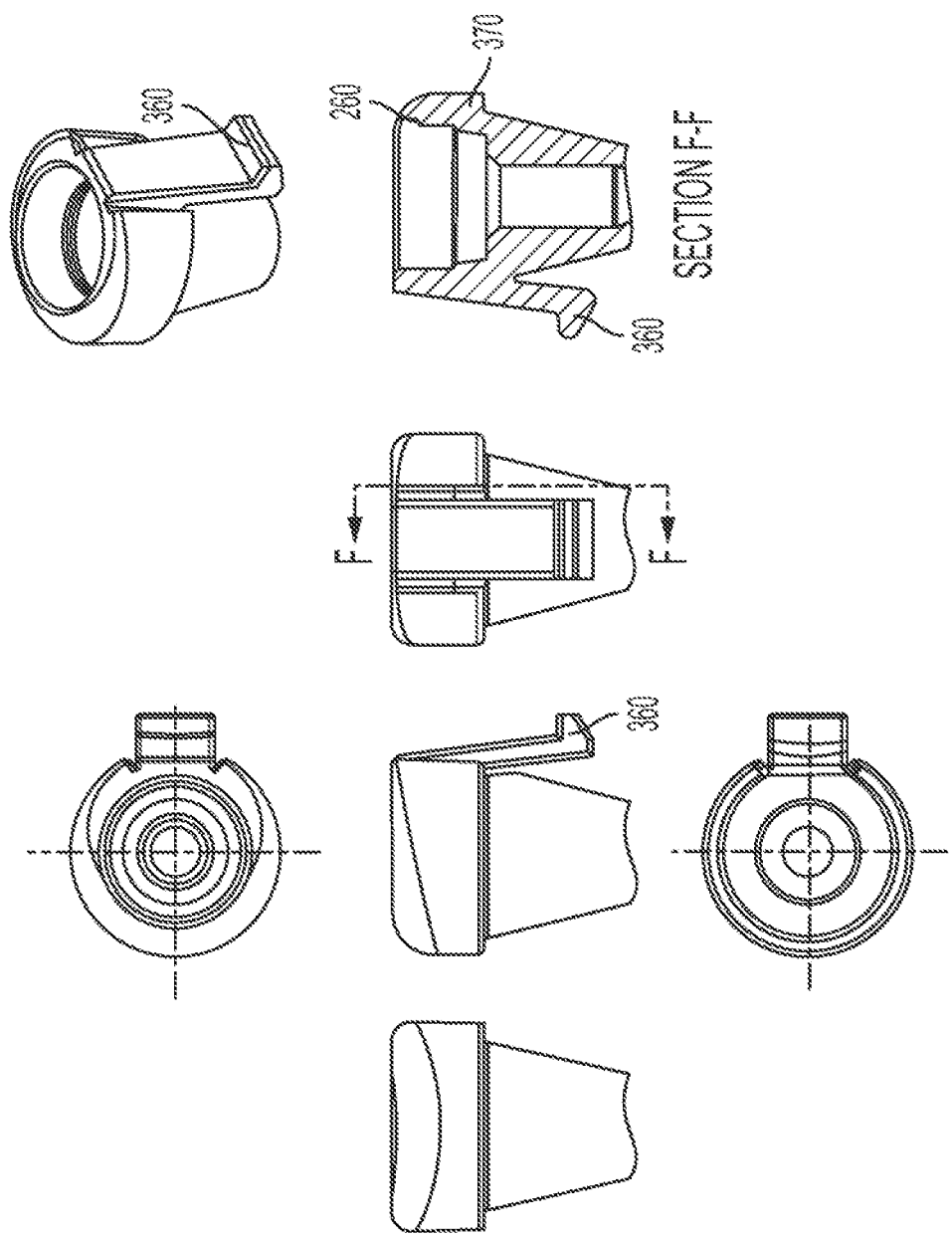
FIG. 29: Depicts an exemplary embodiment of cannula housing.

FIG. 29 depicts an embodiment of a cannula housing 260. The cannula housing has a tab 360 that is flexible and can bend to fit under a protrusion portion of the upper base part. The cannula housing has a protrusion part 370 on an opposite side to the tab 360 that can fit into a recessed portion of the upper base part. The tab 360 and the protrusion part 370 help the cannula housing to maintain its orientation and position when the cannula device is inserted into the housing parts. The cannula housing has a central lumen that narrows in increments toward the lower base part when assembled together. The narrowing provides a secure fluid seal and maintains orientation of the cannula device in the cannula housing.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. An infusion set, comprising:
   a base having an opening to receive a cannula device, the base comprising a lower base part and an upper base part, wherein the upper base part is coupled to the lower base part and is rotatable relative to the lower base part; and
   a connector comprising a fluid connector tube, wherein the fluid connector tube is in fluid connection with the cannula device when the connector is coupled to the base;
   wherein, with the connector coupled to the base, relative rotation of the upper base part and the lower base part is restricted but not prevented.

2. The infusion set of claim 1, wherein the lower base part does not substantially move once the cannula device is in place.

3. The infusion set of claim 1, wherein the lower base part comprises at least three guiding protrusions that are formed on a skin-facing side of the lower base part.

4. The infusion set of claim 1, wherein the guiding protrusions are radially symmetric.

5. The infusion set of claim 1, wherein the lower base part comprises a groove;
   wherein the connector comprises a locking protrusion; and
   wherein the groove receives the locking protrusion when the connector is coupled to the base.

6. The infusion set of claim 1, wherein the upper base part comprises a rotatable connection;
   wherein the lower base part comprises a rotation groove; and
   wherein the rotatable connection sits and rotates in the rotation groove.

7. The infusion set of claim 1, wherein the lower base part comprises a clear portion configured to provide a view of user skin.

8. The infusion set of claim 1, wherein the lower base part comprises a plurality of grooves; and
   wherein each groove is configured to receive a locking protrusion of the connector to thereby restrict relative rotation of the upper base part and the lower base part without preventing relative rotation of the upper base part and the lower base part.

9. The infusion set of claim 8, wherein the plurality of grooves comprises no more than ten grooves.

10. An infusion set, comprising:
    a base having an opening to receive a cannula device, the base comprising:
    a first base part comprising a plurality of grooves; and
    a second base part rotatably coupled with the first base part; and
    a connector comprising a fluid connector tube and a locking protrusion;

wherein, with the connector coupled to the base, the fluid connector tube is in fluid communication with the opening; and wherein, with the connector coupled to the base, the locking protrusion is received in one of the grooves to thereby limit relative rotation of the first base part and the second base part without preventing relative rotation of the first base part and the second base part.

11. The infusion set of claim 10, wherein the first base part further comprises a plurality of guide protrusions separating the plurality of grooves.

12. The infusion set of claim 10, wherein the first base part is a lower base part and the second base part is an upper base part.

13. The infusion set of claim 10, wherein the second base part comprises two openings in fluid communication with the cannula device; and wherein each opening of the two openings is covered by a corresponding and respective membrane.

14. The infusion set of claim 10, wherein one of the first base part or the second base part comprises an adhesive configured to secure the base to skin of a user.

15. An infusion set, comprising:
a base having an opening to receive a cannula device, the base comprising:
a first base part comprising a plurality of guide protrusions; and
a second base part rotatably coupled with the first base part; and a connector comprising a fluid connector tube and a locking protrusion;

wherein, with the connector coupled to the base, the fluid connector tube is in fluid communication with the opening; and wherein, with the connector coupled to the base, the locking protrusion is received between two of the guide protrusions such that relative rotation of the first base part and the second base part is restricted but not prevented.

16. The infusion set of claim 15, wherein, with the connector removed from the base, the first base part and the second base part are capable of rotating through 360° relative to one another.

17. The infusion set of claim 15, wherein the first base part comprises no more than ten of the guide protrusions.

18. The infusion set of claim 15, wherein, with the connector coupled to the base, the first base part and the second base part are limited to relative rotation in a range of 5° to 45°.

19. The infusion set of claim 15, wherein the plurality of guide protrusions are evenly angularly spaced.

20. The infusion set of claim 15, wherein at least one of the first base part or the second base part comprises a lip configured to engage the other of the first base part or the second base part to thereby discourage separation of the first base part and the second base part.

* * * * *